United States Patent
Maldonado et al.

(10) Patent No.: US 11,590,079 B2
(45) Date of Patent: Feb. 28, 2023

(54) TREATING MICROVASCULAR DYSFUNCTION

(71) Applicant: EndoProtech, Inc., Louisville, KY (US)

(72) Inventors: Claudio Maldonado, Louisville, KY (US); Phillip Bauer, Louisville, KY (US)

(73) Assignee: EndoProtech, Inc., Louisville, KY (US)

(*) Notice: Subject to any disclaimer, the term of this patent is extended or adjusted under 35 U.S.C. 154(b) by 0 days.

(21) Appl. No.: 16/962,956

(22) PCT Filed: Jan. 18, 2019

(86) PCT No.: PCT/US2019/014239
§ 371 (c)(1),
(2) Date: Jul. 17, 2020

(87) PCT Pub. No.: WO2019/143969
PCT Pub. Date: Jul. 25, 2019

(65) Prior Publication Data
US 2020/0338003 A1 Oct. 29, 2020

Related U.S. Application Data

(60) Provisional application No. 62/618,679, filed on Jan. 18, 2018.

(51) Int. Cl.
*A61K 9/127* (2006.01)
*A61P 9/10* (2006.01)
(Continued)

(52) U.S. Cl.
CPC .......... *A61K 9/1271* (2013.01); *A61K 9/0019* (2013.01); *A61K 31/685* (2013.01);
(Continued)

(58) Field of Classification Search
CPC .. A61K 9/1271; A61K 9/0019; A61K 31/685; A61K 9/127; A61P 9/10;
(Continued)

(56) References Cited

U.S. PATENT DOCUMENTS 5,866,135 A * 2/1999 Blake .................. A61K 39/092
424/197.11
6,217,899 B1 4/2001 Benameur et al.
(Continued)

FOREIGN PATENT DOCUMENTS

| EP | 2 123 258 | * 11/2009 |
| EP | 2123258 | 11/2009 |
| WO | WO2016022547 A1 | 2/2016 |

OTHER PUBLICATIONS

Eckert, G.P., et al in Biochimica Biophysica Acta, vol. 1808, pp. 236-243, 2011.*
(Continued)

*Primary Examiner* — Gollamudi S Kishore
(74) *Attorney, Agent, or Firm* — Fish & Richardson P.C.

(57) ABSTRACT

The present disclosure relates to compositions comprising phospho-lipids, lipid vesicles, and/or liposomes, and methods of use thereof. In one aspect, the present disclosure relates to methods and compositions for delivery of, biologically active lipids to reduce microvascular dysfunction and infarct size during revascularization of the blocked artery in a mammalian subject.

8 Claims, 10 Drawing Sheets

A.

B.

(51) Int. Cl.
  A61K 9/00    (2006.01)
  A61K 31/685  (2006.01)
  A61M 25/00   (2006.01)
(52) U.S. Cl.
  CPC ............... *A61P 9/10* (2018.01); *A61M 25/00* (2013.01); *A61M 2210/12* (2013.01)
(58) Field of Classification Search
  CPC .............. A61M 25/00; A61M 2210/12; G01N 33/5438; G01N 27/026; G01N 27/3276; C07K 5/1019; C07K 5/1021; C07K 7/06
  See application file for complete search history.

(56) References Cited

U.S. PATENT DOCUMENTS

| | | | |
|---|---|---|---|
| 6,468,798 B1 | 10/2002 | Debs et al. | |
| 7,220,538 B2 | 5/2007 | Fischer et al. | |
| 7,339,042 B2* | 3/2008 | Sullivan | A61K 48/0058 536/23.1 |
| 2003/0026831 A1* | 2/2003 | Lakkaraju | C12N 15/1135 424/450 |
| 2003/0060415 A1 | 3/2003 | Hung | |
| 2003/0185794 A1 | 10/2003 | Colley | |
| 2005/0020522 A1 | 1/2005 | Laguens | |
| 2005/0113297 A1* | 5/2005 | Francois | A61P 35/00 424/155.1 |
| 2005/0118250 A1* | 6/2005 | Tardi | A61P 43/00 424/450 |
| 2007/0286898 A1* | 12/2007 | Takagi | A61K 9/1271 424/450 |
| 2010/0021531 A1 | 1/2010 | Yoshino et al. | |
| 2011/0182979 A1* | 7/2011 | Shimoda | A61P 1/16 424/450 |
| 2011/0229529 A1 | 9/2011 | Irvine | |
| 2012/0010557 A1* | 1/2012 | Heger | A61K 9/1272 604/20 |
| 2013/0195969 A1 | 8/2013 | Geall | |
| 2013/0337545 A1* | 12/2013 | Sabbadini | C12N 15/70 435/252.3 |
| 2015/0056269 A1* | 2/2015 | Chaimbault | A61P 9/00 424/450 |
| 2015/0147383 A1 | 5/2015 | Sahebkar et al. | |
| 2016/0120807 A1 | 5/2016 | Maldonado | |
| 2016/0369001 A1* | 12/2016 | Sonoda | C12Y 301/06013 |

OTHER PUBLICATIONS

Blaho et al., "An update on the biology of sphingosine 1-phosphate receptors," Journal of Lipid Research, Aug. 1, 2014, 55(8):1596-608.
Bode et al, "Erythrocytes serve as a reservoir for cellular and extracellular sphingosine 1-phosphate," Journal of Cellular Biochemistry, Apr. 15, 2010, 109(6):1232-43.
Bolognese et al., "Impact of microvascular dysfunction on left ventricular remodeling and long-term clinical outcome after primary coronary angioplasty for acute myocardial infarction," Circulation, Mar. 9, 2004, 109(9):1121-6.
Durante et al., "Novel insights into an "old" phenomenon: the no reflow," International Journal of Cardiology, May 6, 2015, 187:273-80.
Feher et al., "Prevention and treatment of no-reflow phenomenon by targeting the coronary microcirculation," Reviews in Cardiovascular Medicine, Jan. 1, 2014, 15(1):38-51.
Francone et al., "Impact of primary coronary angioplasty delay on myocardial salvage, infarct size, and microvascular damage in patients with ST-segment elevation myocardial infarction: insight from cardiovascular magnetic resonance," Journal of the American College of Cardiology, Dec. 1, 2009, 54(23):2145-53.
Hanson et al., "Crystal structure of a lipid G protein—coupled receptor." Science, Feb. 17, 2012, 335(6070):851-5.
Huang et al., "Efficacy of intracoronary nicardipine in the treatment of no-reflow during percutaneous coronary intervention," Catheterization and Cardiovascular Interventions, Nov. 2006, 68(5):671-6.
IUPAC-IUB Commission on Bio-Chemical Nomenclature, "Symbols for Amino-Acid Derivatives and Peptides: Recommendations," Biochemistry, Apr. 1, 1972, 11(9), 1726-1732.
Iwakura et al., "Nicorandil treatment in patients with acute myocardial infarction," Circulation Journal, May 2009, 73(5):925-31.
Lichtenberg et al., "Liposomes: preparation, characterization, and preservation," Methods in Biochemical Analysis, Jan. 1, 1988, 33:337-462.
Mahaffey et al., "Adenosine as an adjunct to thrombolytic therapy for acute myocardial infarction: results of a multicenter, randomized, placebo-controlled trial: the Acute Myocardial Infarction STudy of ADenosine (AMISTAD) trial," Journal of the American College of Cardiology, Novemeber 15, 1999, 34(6):1711-20.
McAlindon et al., "Infarct size reduction in acute myocardial infarction," Heart, Jan. 15, 2015, 101(2):155, 9 pages.
PCT International Preliminary Report on Patentability in International Appln. No. PCT/US2019/014239, dated Jul. 21, 2020, 7 pages.
Reffelmann et al., "The 'no-reflow' phenomenon: basic science and clinical correlates," Heart, Feb. 1, 2002, 87(2):162-8.
Rezkalla et al., "Management of no-reflow phenomenon in the catheterization laboratory," JACC: Cardiovascular Interventions, Feb. 6, 2017, 10(3):215-23.
Ross et al., "AMISTAD-II Investigators. A randomized, double-blinded, placebo-controlled multicenter trial of adenosine as an adjunct to reperfusion in the treatment of acute myocardial infarction (AMISTAD-II)," Journal of the American College of Cardiology, Jun. 7, 2005, 45(11):1775-80.
Uitterdijk et al., "Serial measurement of hFABP and high-sensitivity troponin I post-PCI in STEMI: how fest and accurate can myocardial infarct size and no-reflow be predicted?," American Journal of Physiology-Heart and Circulatory Physiology, Oct. 1, 2013, 305(7):H1104-10.
US Department of Health and Human Services, "State Program Injury Indicators Report, Fourth Edition—2005 Data," CPC and NCIPC Publication, Jan. 2009, 108 pages.
Zeng et al., "Sphingosine-1-phosphate protects endothelial glycocalyx by inhibiting syndecan-1 shedding," American Journal of Physiology—Heart and Circulatory Physiology, Feb. 1, 2014, 306(3):H363-72.
Authorized officer Lee W. Young, International Search Report/Written Opinion in PCT/US2019/014239 dated Apr. 8, 2019, 13pages.
Di Nezza et al., "Liposomes as a putative tool to investigate NAADP signaling in vasculogenesis," Journal of Cellular Biochemistry, Nov. 2017, 118(11):3722-9.
EP European Search Report in European Appln. No. 19741045.9, dated Mar. 21, 2021, 11 pages.
Goga et al., "A novel liposome-based therapy to reduce complement-mediated injury in revascularized tissues," Journal of Surgical Research, Jan. 1, 2011, 165(1):e51-7.

* cited by examiner

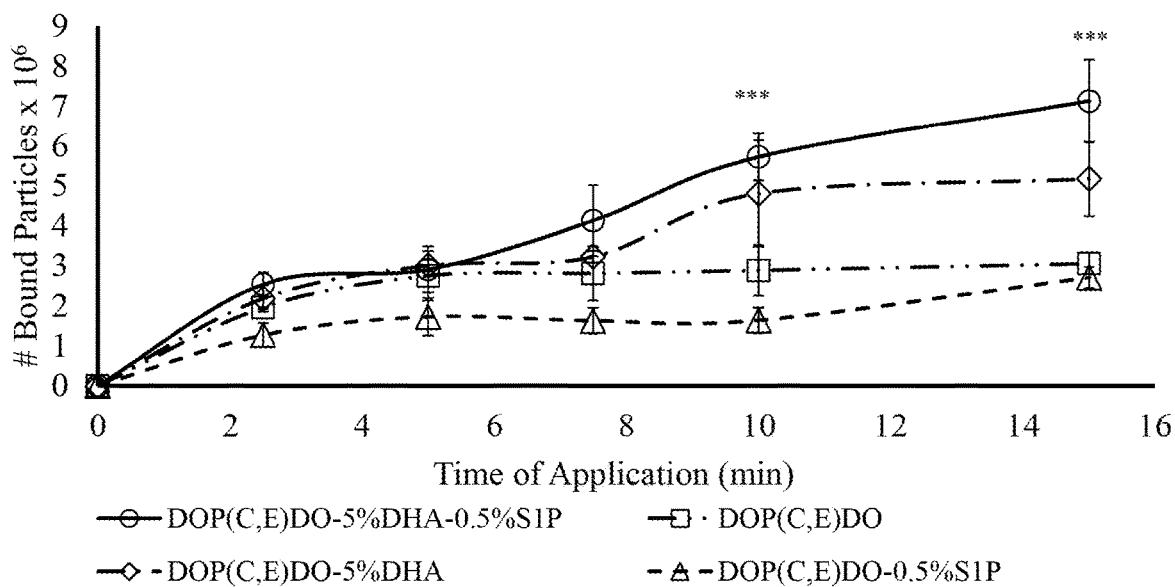
FIGS. 2A-2B
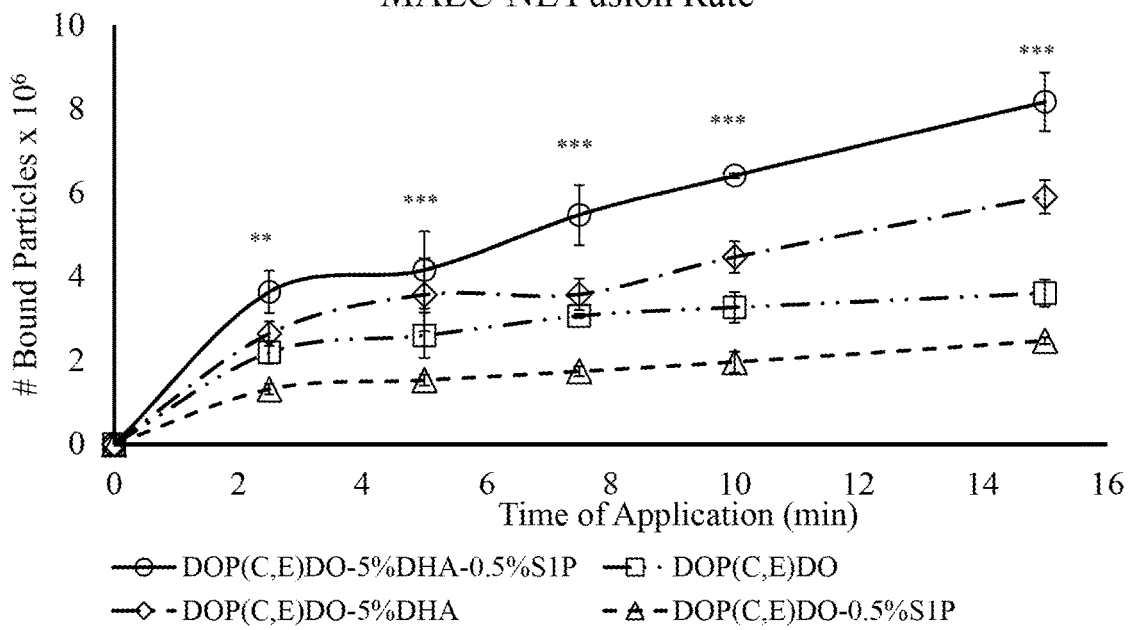

FIG. 9

Effect of Treatment on Mean Clinical Chemistry

| Group | Gender | Statistic | Albumin g/dL | A/G | Alk Phos U/L | Urea N[2] mg/dL | P mg/dL | Glucose mg/dL | Cl mEq/dL |
|---|---|---|---|---|---|---|---|---|---|
| 1A (PBS) | Female | Mean | 2.6 | 1.2 | 128 | 23 | 8.4 | 163 | 114 |
| | | SD | 0.1 | 0.1 | 18 | 2 | 0.5 | 14 | 2 |
| 1B (PBS) | Male | Mean | 2.4 | 1.0 | 93 | 18 | 7.8 | 192 | 110 |
| | | SD | 0.1 | 0.1 | 14 | 2 | 0.9 | 32 | 1 |
| | | P-value vs 1A | 0.06 | 0.004 | 0.01 | 0.002 | 0.24 | 0.11 | 0.001 |
| 2A (180mg/kg) | Female | Mean | 2.8 | 1.4 | 156 | 22 | 8.1 | 196 | 117 |
| | | SD | 0.1 | 0.1 | 40 | 5 | 1.4 | 20 | 1 |
| | | P-value vs 1A | 0.03 | 0.004 | 0.19 | 0.68 | 0.71 | 0.02 | 0.01 |
| 2B (180mg/kg) | Male | Mean | 2.5 | 1.0 | 81 | 20 | 8.4 | 169 | 109 |
| | | SD | 0.2 | 0.1 | 14 | 3 | 0.9 | 21 | 3 |
| | | P-value vs 1B | 0.82 | 1.00 | 0.19 | 0.20 | 0.33 | 0.22 | 0.88 |
| 3A (240mg/kg) | Female | Mean | 2.9 | 1.3 | 109 | 22 | 9.0 | 205 | 117 |
| | | SD | 0.2 | 0.1 | 19 | 3 | 1.3 | 30 | 2 |
| | | P-value vs 1A | 0.03 | 0.11 | 0.15 | 0.36 | 0.36 | 0.02 | 0.02 |
| 3B (240mg/kg) | Male | Mean | 2.2 | 0.9 | 59 | 24 | 9.2 | 150 | 109 |
| | | SD | 0.1 | 0.1 | 12 | 3 | 0.2 | 20 | 2 |
| | | P-value vs 1B | 0.003 | 0.03 | 0.003 | 0.004 | 0.01 | 0.04 | 0.86 |

FIG. 10

Effect of Treatment on Mean CBCs

| Group | Gender | Statistic | WBC x10³/μL | RBC x10⁶/μL | Hct % | MCH pg | MCHC g/dL |
|---|---|---|---|---|---|---|---|
| 1A (PBS) | Female | Mean | 4.0 | 10.3 | 53 | 14.7 | 28.3 |
| | | SD | 1.9 | 0.2 | 2 | 0.3 | 0.7 |
| 1B (PBS) | Male | Mean | 6.9 | 10.2 | 53 | 14.4 | 28.0 |
| | | SD | 1.1 | 0.4 | 2 | 0.2 | 0.3 |
| | | P-value vs 1A | 0.02 | 0.76 | 0.67 | 0.14 | 0.33 |
| 2A (180mg/kg) | Female | Mean | 4.4 | 10.6 | 54 | 14.5 | 28.5 |
| | | SD | 2.3 | 0.4 | 2 | 0.3 | 0.3 |
| | | P-value vs 1A | 0.74 | 0.18 | 0.61 | 0.49 | 0.54 |
| 2B (180mg/kg) | Male | Mean | 5.3 | 10.1 | 52 | 14.6 | 28.1 |
| | | SD | 3.8 | 0.6 | 2 | 0.4 | 0.3 |
| | | P-value vs 1B | 0.40 | 0.67 | 0.77 | 0.36 | 0.38 |
| 3A (240mg/kg) | Female | Mean | 9.0 | 10.8 | 54 | 14.4 | 28.7 |
| | | SD | 2.1 | 0.3 | 2 | 0.5 | 0.1 |
| | | P-value vs 1A | 0.004 | 0.02 | 0.56 | 0.27 | 0.26 |
| 3B (240mg/kg) | Male | Mean | 8.9 | 9.0 | 48 | 15.1 | 28.6 |
| | | SD | 3.3 | 0.6 | 4 | 0.6 | 0.4 |
| | | P-value vs 1B | 0.22 | 0.003 | 0.04 | 0.03 | 0.02 |

FIG. 11

Effect of Treatment on Mean Differential WBC Counts

| Group | Gender | Statistic | Platelets x10³/μl | Neutrophils | % | Lymphocytes | % | Monocytes | % |
|---|---|---|---|---|---|---|---|---|---|
| 1A (PBS) | Female | Mean | 1553 | 522 | 128 | 3283 | 83 | 90 | 2 |
|  |  | SD | 149 | 389 | 18 | 1542 | 4 | 60 | 2 |
| 1B (PBS) | Male | Mean | 1540 | 836 | 93 | 5361 | 77 | 526 | 8 |
|  |  | SD | 178 | 262 | 14 | 1125 | 5 | 122 | 1 |
|  |  | P-value vs 1A | 0.90 | 0.90 | 0.17 | 0.04 | 0.12 | 0.001 | 0.0003 |
| 2A (180mg/kg) | Female | Mean | 1279 | 396 | 156 | 3744 | 85 | 206 | 4 |
|  |  | SD | 252 | 353 | 40 | 1865 | 6 | 187 | 3 |
|  |  | P-value vs 1A | 0.07 | 0.07 | 0.61 | 0.68 | 0.41 | 0.41 | 0.39 |
| 2B (180mg/kg) | Male | Mean | 1851 | 884 | 81 | 3849 | 73 | 460 | 7 |
|  |  | SD | 381 | 696 | 14 | 2804 | 7 | 449 | 3 |
|  |  | P-value vs 1B | 0.14 | 0.14 | 0.89 | 0.30 | 0.28 | 0.28 | 0.76 |
| 3A (240mg/kg) | Female | Mean | 1420 | 844 | 109 | 7487 | 83 | 442 | 5 |
|  |  | SD | 289 | 162 | 19 | 1989 | 3 | 259 | 3 |
|  |  | P-value vs 1A | 0.39 | 0.39 | 0.13 | 0.01 | 0.94 | 0.02 | 0.10 |
| 3B (240mg/kg) | Male | Mean | 2741 | 3009 | 59 | 4808 | 56 | 671 | 10 |
|  |  | SD | 867 | 1407 | 12 | 1756 | 9 | 672 | 7 |
|  |  | P-value vs 1B | 0.02 | 0.01 | 0.001 | 0.57 | 0.002 | 0.65 | 0.46 |

FIG. 12

Regional Myocardial Blood Flow

| | RMBF (ml/min/g) | | Control (n=6) | Treated (n=6) | p-value |
|---|---|---|---|---|---|
| Baseline | Non-ischemic zone (NIZ) | Epicardium | 0.63 ± 0.06 | 0.85 ± 0.09 | 0.052 |
| | | Endocardium | 0.50 ± 0.03 | 0.64 ± 0.07 | 0.113 |
| | | Mean | 0.57 ± 0.04 | 0.76 ± 0.08 | 0.062 |
| | Ischemic zone (IZ) | Epicardium | 0.63 ± 0.07 | 0.80 ± 0.07 | 0.127 |
| | | Endocardium | 0.47 ± 0.05 | 0.64 ± 0.07 | 0.079 |
| | | Mean | 0.55 ± 0.06 | 0.72 ± 0.07 | 0.097 |
| | IZ:NIZ ratio | | 0.96 ±0.06 | 0.97 ± 0.06 | 0.880 |
| 45' Occlusion | Non-ischemic zone (NIZ) | Epicardium | 0.66 ± 0.25 | 0.80 ± 0.13 | 0.623 |
| | | Endocardium | 0.60 ± 0.26 | 0.55 ± 0.06 | 0.863 |
| | | Mean | 0.63 ± 0.25 | 0.68 ± 0.09 | 1.000 |
| | Ischemic zone (IZ) | Epicardium | 0.00 ± 0.00 | 0.00 ± 0.00 | NA |
| | | Endocardium | 0.00 ± 0.00 | 0.00 ± 0.00 | NA |
| | | Mean | 0.00 ± 0.00 | 0.00 ± 0.00 | NA |
| | IZ:NIZ ratio | | 0.00 ±0.00 | 0.00 ± 0.00 | NA |
| 15' Reperfusion | Non-ischemic zone (NIZ) | Epicardium | 0.53 ± 0.11 | 0.86 ± 0.28 | 0.295 |
| | | Endocardium | 0.46 ± 0.09 | 0.59 ± 0.17 | 0.544 |
| | | Mean | 0.50 ± 0.10 | 0.72 ± 0.22 | 0.378 |
| | Ischemic zone (IZ) | Epicardium | 0.61 ± 0.21 | 2.41 ± 0.66 | 0.028* |
| | | Endocardium | 0.78 ± 0.15 | 2.08 ± 0.56 | 0.050* |
| | | Mean | 0.70 ± 0.18 | 2.24 ± 0.61 | 0.034* |
| | IZ:NIZ ratio | | 1.35 ±0.20 | 3.31 ± 0.72 | 0.025* |
| 72h Reperfusion | Non-ischemic zone (NIZ) | Epicardium | 0.88 ± 0.23 | 1.09 ± 0.24 | 0.524 |
| | | Endocardium | 0.68 ± 0.15 | 0.82 ± 0.14 | 0.514 |
| | | Mean | 0.78 ± 0.18 | 0.96 ± 0.19 | 0.506 |
| | Ischemic zone (IZ) | Epicardium | 0.96 ± 0.31 | 1.14 ± 0.20 | 0.629 |
| | | Endocardium | 0.85 ± 0.26 | 0.97 ± 0.16 | 0.725 |
| | | Mean | 0.91 ± 0.28 | 1.05 ± 0.14 | 0.645 |
| | IZ:NIZ ratio | | 1.13 ±0.33 | 1.28 ± 0.23 | 0.719 |

TREATING MICROVASCULAR DYSFUNCTION

CLAIM OF PRIORITY

This application is a 371 U.S. National Application of PCT/US2019/014239 filed Jan. 18, 2019, which claims the benefit of U.S. Provisional Application No. 62/618,679, filed on Jan. 18, 2018. The entire contents of the foregoing are incorporated herein by reference.

FEDERALLY SPONSORED RESEARCH OR DEVELOPMENT

This invention was made with government support under Grant No. HL132649 awarded by the National Institutes of Health. The Government has certain rights in the invention.

TECHNICAL FIELD

The present disclosure relates to relates to compositions comprising phospholipids, lipid vesicles, and/or liposomes, and methods of use thereof.

BACKGROUND

Ischemic heart disease (IHD), the leading cause of death and disability worldwide, affects 17,600,000 Americans. According to the CDC, 611,105 Americans died of heart disease in 2013, with approximately 450,000 attributed to IHD. Globally, the World Health Organization reports that IHD causes 7.2 million deaths each year. Myocardial infarction causes the greatest mortality and morbidity in cardiac patients with IHD.

Several mechanical-pharmacological methods to reduce infarct size following ST-segment elevation myocardial infarction (STEMI) have been developed.[1] Of these, percutaneous coronary intervention (PCI) within 120 minutes of first medical contact is the recommended reperfusion therapy for STEMI. Two factors support the PCI approach: (1) prognosis following PCI has consistently been shown to be superior to fibrinolysis in patients with STEMI, due to a reduction in infarct size,[1] and (2) delaying reperfusion results in a larger infarct size.[2] Unfortunately, depending on the severity of ischemia, infarct expansion occurs up to 48 h following revascularization, and this occurrence has been attributed to the "no-reflow" phenomenon.[3-6]

Currently, no proven therapies to treat coronary microvascular no-reflow are supported by large randomized clinical trials. The most difficult obstacle to such treatments is the delivery of therapeutic concentrations of agents to the sites of microvascular dysfunction. Large clinical trials evaluated the effect of IV adenosine and other agents with no success.[7-8]

SUMMARY

The present disclosure provides methods and compositions for delivery of, biologically active lipids to reduce microvascular dysfunction and infarct size during revascularization of the blocked artery in a mammalian subject. In one aspect, the disclosure relates to administering oleic acid phospholipids, lysosphingolipids and polyunsaturated lipids in effective amounts to reduce an anatomic zone of no-reflow in subjects in need thereof.

In one aspect, the disclosure relates to a composition comprising a plurality of nanoliposomes (NL). In some embodiments, the nanoliposomes comprise one or more negatively charged phospholipids and one or more neutrally charged phospholipids. In some embodiments, the neutrally charged phospholipids are selected from the group consisting of phosphatidylcholine (PC) and phosphatidylethanolamine (PE), or a combination thereof, and the negatively charged phospholipids are selected from the group consisting of phosphatidic acid (PA), phosphatidylserine (PS), and phosphatidylgylcerol (PG), or a combination thereof.

In some embodiments, the plurality of nanoliposomes have an average diameter of about 50 nm to about 250 nm.

In some embodiments, the PC is 14:1 ($\Delta$9-Cis) PC—1,2-dimyristoleoyl-sn-glycero-3-phosphocholine, 16:1 ($\Delta$9-Cis) PC—1,2-dipalmitoleoyl-sn-glycero-3-phosphocholine, 18:1 ($\Delta$9-Cis) PC (DOPC)—1,2-dioleoyl-sn-glycero-3-phosphocholine, 20:1 ($\Delta$11-Cis) PC—1,2-dieicosenoyl-sn-glycero-3-phosphocholine, 22:1 ($\Delta$13-Cis) PC—1,2-dierucoyl-sn-glycero-3-phosphocholine, 24:1 ($\Delta$15-Cis) PC—1,2-dinervonoyl-sn-glycero-3-phosphocholine, or a combination thereof.

In some embodiments, the PE is 16:1 ($\Delta$9-Cis) PE-1,2-dipalmitoleoyl-sn-glycero-3-phosphoethanolamine, 18:1 ($\Delta$9-Cis) PE (DOPE)-1,2-dioleoyl-sn-glycero-3-phosphoethanolamine, or a combination thereof.

In some embodiments, the PA is 18:1 PA (DOPA)-1,2-dioleoyl-sn-glycero-3-phosphate, the PS is 18:1 ($\Delta$9-Cis) PS (DOPS)—1,2-dioleoyl-sn-glycero-3-phosphoserine, and the PG is 18:1 ($\Delta$9-Cis) PG-1,2-dioleoyl-sn-glycero-3-phosphoglycerol.

In some embodiments, a molar ratio of the neutrally charged phospholipids to the negatively charged phospholipids is between 5:1 and 1:1.

In some embodiments, the nanoliposomes comprise a polyunsaturated fatty acid (PUFA). In some embodiments, the PUFA is docosahexaenoic acid (DHA), arachidonic acid (AA), eicosapentaenoic acid (EPA), or a combination thereof.

In some embodiments, the nanoliposomes further comprise a lysosphingolipid.

In some embodiments, the nanoliposomes further comprise sphingosine-1-phosphate (S1P), its analog, or a combination thereof.

In some embodiments, the nanoliposomes comprise 1,2-dioleoyl-sn-glycero-3-phosphate (DOPA), 1,2-Dioleoyl-sn-glycerol-3-phosphocholine (DOPC), 1,2-dioleoyl-sn-glycero-3-phosphoethanolamine (DOPE), DHA and S1P.

In some embodiments, the composition further comprises Ringer's lactate solution.

In one aspect, the disclosure relates to a method for treating microvascular dysfunction or treating disorders or injuries associated with microvascular no-reflow phenomenon, the method comprising administering an effective amount of the composition described herein, to a subject in need thereof. In some embodiments, the nanoliposomes are incorporated into cell membranes of endothelial cells of the subject.

In some embodiments, the composition is administered to the subject prior to a revascularization procedure, after a revascularization procedure, during and after a revascularization procedure, or continuously before, during, and after a revascularization procedure.

In some embodiments, the composition is administered to the subject intra-arterially while a catheter is positioned in the ischemia related artery prior to the formation of the anatomic zone of no-reflow.

In some embodiments, the composition is administered into the anatomic zone of no-reflow by using Ringer's lactate at physiological pH as the vehicle.

In some embodiments, 5 mg to 200 mg of nanoliposomes are administered into the anatomic zone of no-reflow.

In some embodiments, the phospholipids has a concentration of about 1 to about 20 mg/mL in the composition, and about 5 to about 10 ml of the composition is administered into the anatomic zone of no-reflow.

In some embodiments, the method reduces an anatomic zone of no-reflow.

In one aspect, the disclosure relates to a method for increasing blood flow during revascularization, treating microvascular no-reflow phenomenon in tissues affected by the revascularization of a blocked artery, reducing an anatomic zone of no-reflow, stabilizing and maintaining microvascular barrier function, inhibiting endothelial cell activation, reducing microvascular dysfunction, or reducing infarct size during revascularization, the method comprising administering a therapeutic effective amount of a composition comprising monounsaturated phospholipids to a subject in need thereof.

In some embodiments, the composition comprises a plurality of nanoliposomes (NL) comprising monounsaturated phospholipids. In some embodiments, the plurality of nanoliposomes have an average diameter of about 50 nm to about 150 nm. In some embodiments, the nanoliposomes comprise a negatively charged phospholipid and a neutrally charged phospholipid.

In one aspect, the disclosure relates to use of a composition for increasing blood flow during revascularization, treating microvascular no-reflow phenomenon in tissues affected by the revascularization of a blocked artery, reducing an anatomic zone of no-reflow, stabilizing and maintaining microvascular barrier function, inhibiting endothelial cell activation, reducing microvascular dysfunction, or reducing infarct size during revascularization. In some embodiments, the composition comprises monounsaturated phospholipids.

In one aspect, the disclosure relates to use of a composition for increasing blood flow during revascularization, treating microvascular no-reflow phenomenon in tissues affected by the revascularization of a blocked artery, reducing an anatomic zone of no-reflow, stabilizing and maintaining microvascular barrier function, inhibiting endothelial cell activation, reducing microvascular dysfunction, or reducing infarct size during revascularization. In some embodiments, the composition comprises a plurality of nanoliposomes (NL), wherein the nanoliposomes comprise one or more negatively charged phospholipids and one or more neutrally charged phospholipids, wherein the neutrally charged phospholipids are selected from the group consisting of phosphatidylcholine (PC) and phosphatidylethanolamine (PE), or a combination thereof, and the negatively charged phospholipids are selected from the group consisting of phosphatidic acid (PA), phosphatidylserine (PS), and phosphatidylglycerol (PG), or a combination thereof.

In one aspect, the disclosure also provides the use of the compositions described herein for the manufacture of a medicament for increasing blood flow during revascularization, treating microvascular no-reflow phenomenon in tissues affected by the revascularization of a blocked artery, reducing an anatomic zone of no-reflow, stabilizing and maintaining microvascular barrier function, inhibiting endothelial cell activation, reducing microvascular dysfunction, or reducing infarct size during revascularization.

In one aspect, the disclosure relates to a composition for treating a microvascular no-reflow phenomenon in tissues affected by the revascularization of a blocked artery. The composition can include a plurality of bioactive monounsaturated phospholipids.

In some embodiments, the lipids are made into a nanoliposome (NL) with an average diameter of about 50 nm to 150 nm.

In some embodiments, the NL comprises negatively charged phospholipids and neutrally charged phospholipids.

In some embodiments, the neutrally charged phospholipids are selected from the group consisting of phosphatidylcholine (PC) and phosphatidylethanolamine (PE), selected from the groups consisting of:

PC:
- 14:1 (Δ9-Cis) PC—1,2-dimyristoleoyl-sn-glycero-3-phosphocholine
- 16:1 (Δ9-Cis) PC—1,2-dipalmitoleoyl-sn-glycero-3-phosphocholine
- 18:1 (Δ9-Cis) PC (DOPC)—1,2-dioleoyl-sn-glycero-3-phosphocholine
- 20:1 (Δ11-Cis) PC—1,2-dieicosenoyl-sn-glycero-3-phosphocholine
- 22:1 (Δ13-Cis) PC—1,2-dierucoyl-sn-glycero-3-phosphocholine
- 24:1 (Δ15-Cis) PC—1,2-dinervonoyl-sn-glycero-3-phosphocholine PE:
- 16:1 (Δ9-Cis) PE-1,2-dipalmitoleoyl-sn-glycero-3-phosphoethanolamine
- 18:1 (Δ9-Cis) PE (DOPE)-1,2-dioleoyl-sn-glycero-3-phosphoethanolamine or a combination thereof, and, the negatively charged phospholipids are selected from the group consisting of phosphatidic acid (PA), phosphatidylserine (PS), and phosphatidylglycerol (PG), selected from the groups consisting of:

PA: 18:1 PA (DOPA)—1,2-dioleoyl-sn-glycero-3-phosphate

PS: 18:1 (Δ9-Cis) PS (DOPS)—1,2-dioleoyl-sn-glycero-3-phosphoserine

PG: 18:1 (Δ9-Cis) PG—1,2-dioleoyl-sn-glycero-3-phosphoglycerol or a combination thereof.

In some embodiments, a molar ratio of the neutrally charged phospholipids to the negatively charged phospholipids is between 5:1 and 1:1.

In some embodiments, a polyunsaturated fatty acid (PUFA) is added to increase NL fusogenicity to cells.

In some embodiments, the PUFA is docosahexaenoic acid (DHA), arachidonic acid (AA), eicosapentaenoic acid (EPA), or a combination thereof.

In some embodiments, the composition further comprises a lysosphingolipid to increase NL fusogenicity to cells and stabilize endothelial cells.

In some embodiments, the lysosphingolipid is sphingosine-1-phosphate (S1P) its analog, or a combination thereof.

In some embodiments, the NL lipotherapy comprises 1,2-dioleoyl-sn-glycero-3-phosphate (DOPA), 1,2-Dioleoyl-sn-glycerol-3-phosphocholine (DOPC), 1,2-dioleoyl-sn-glycero-3-phosphoethanolamine (DOPE), DHA and S1P.

In one aspect, the disclosure relates to methods for reducing an anatomic zone of no-reflow in a subject in need thereof. The methods involve the administration of the composition described herein, and incorporating biologically active lipids into endothelial cell membranes to stabilize and maintain microvascular barrier function following a revascularization procedure, thereby reducing an anatomical zone of no-reflow in the subject.

In some embodiments, the subject is administered the NL lipotherapy prior to the revascularization procedure, after the revascularization procedure, during and after the revascularization procedure or continuously before, during, and after the revascularization procedure.

In some embodiments, the subject is administered the NL lipotherapy intra-arterially while a catheter is positioned in the ischemia related artery prior to the formation of the anatomic zone of no-reflow.

In some embodiments, the subject is administered the NL lipotherapy into the anatomic zone of no-reflow, using Ringer's lactate at physiological pH as the vehicle.

In some embodiments, the subject is administered 10 mL of NL lipotherapy containing 10 mg/mL of lipid into the anatomic zone of no-reflow.

In some embodiments, the subject is administered about 5-10 mL of NL lipotherapy containing about 1-20 mg/mL of lipid into the anatomic zone of no-reflow.

As used herein, the term "bioactive lipid" refers to a lipid that serves as a ligand to a cell receptor and/or a lipid that when incorporated into a cell membrane, via liposome fusion, alters the membrane composition that surrounds a receptor's transmembrane domain and modulates its function.

As used herein, the term "revascularization" refers to the re-opening of an occluded artery (e.g., percutaneous transluminal coronary angioplasty, insertion of a bypass graft, insertion of a stent, administration of a thrombolytic agent, etc.) to re-establish blood flow to an ischemic tissue As used herein, the term "monounsaturated fatty acid" refers to a fatty acid containing one carbon-carbon double bond. In some embodiments, the monounsaturated fatty acid is a cis monounsaturated fatty acid and has one cis carbon-carbon double bond. In some embodiments, the monounsaturated fatty acid a trans monounsaturated fatty acid and has one trans carbon-carbon double bond.

As used herein, the term "monounsaturated phospholipid" refers to a lipid containing a phosphate as part of the head group and two monounsaturated fatty acids as tail groups.

As used herein, the term "polyunsaturated fatty acid (PUFA)" refers to a fatty acid with 2 or more carbon-carbon double bonds. In some embodiments, the PUFA has 2 or more cis carbon-carbon double bonds. In some embodiments, the PUFA has 2 or more trans carbon-carbon double bonds.

As used herein, the term "hydration" refers to a process of adding water or a water based solution (i.e., phosphate buffer saline (PBS), Ringer's lactate, physiological solutions) to a mixture of lipids. In some embodiments, the lipids are phospholipids.

As used herein, the term "hydrating solution" refers to an aqueous solution containing water-soluble components used in the hydration process.

As used herein, the term "lipid soluble component" refers to a compound that has a high solubility in organic solvents, or a considerably higher solubility in organic solvents than compared to water.

As used herein, the term "lipid vesicle" refers to a lipid-based construct. In some embodiments, a lipid vesicle is a liposome.

As used herein, the term "liposome" or "lipid vesicles" refers to a lipid based construct having a lipid bilayer which separates an aqueous compartment inside from the aqueous exterior.

As used herein, the term "nanoliposome" refers to a liposome with the diameter that is in the range of about 1 nm to about 1000 nm. In some embodiments, the nanoliposomes have a diameter of about 50 nm to about 250 nm. In some embodiments, the nanoliposomes have a diameter of about 50 nm to about 150 nm.

As used herein, the term "lysosphingolipid" refers to a sphingosine based lipid with a phosphate head group and no fatty acid component.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the methods described herein.

As used herein, the ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

Unless otherwise indicated, all numbers expressing quantities of ingredients, properties such as reaction conditions, and so forth used in the specification are to be understood to disclose "about" that particular value in addition to the value itself. Accordingly, unless indicated to the contrary, the numerical parameters set forth in this specification include approximations that can vary depending upon the desired properties sought to be obtained by the presently-disclosed subject matter.

As used herein, the abbreviations for any lipids, and other compounds, are, unless indicated otherwise, in accord with their common usage, recognized abbreviations, or the IUPAC-IUB Commission on Biochemical Nomenclature (see, Biochem. (1972) 11(9):1726-1732).

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF THE DRAWINGS

FIGS. 2A-2B. Fusion kinetic studies performed on mouse aortic endothelial cells (MAECs) and pig coronary arterial endothelial cells (PCAECs) demonstrated that nanoliposomes (NL) lipotherapy formulations containing 0.5% S1P, hydrated with PBS, had an enhanced fusion rate with cells when the formulation included 5% DHA. The rate of NL lipid incorporation into PCAECs (A) and MAECs (B) was faster in the S1P/DHA formulated vesicles. NLs were labeled with rhodamine for fluorescent detection. NL formulations were the following: DOP(C,E)DO=DOPC, DOPA, DOPE, 1.8:2.4:1 molar ratio; DOP(C,E)DO 5% DHA=DOPC, DOPA, DOPE, 1.8:2.4:1 molar ratio, with 5% DHA by weight; DOP(C,E)DO 0.5% S1P=DOPC, DOPA, DOPE, 1.8:2.4:1 molar ratio, with 0.5% SP by weight; DOP(C,E)DO 5% DHA, 0.5% S1P=DOPC, DOPA, DOPE, 1.8:2.4:1 molar ratio, with 5% DHA and 0.5% SW by weight. Values are mean±SEM; *P<0.05 vs. all groups; #P<0.05 vs. DOP(C,E)DO and DOP(C,E)DO 0.5% S1P.

FIG. 9. Effect of treatment on mean clinical chemistry.

FIG. 10. Effect of treatment on mean complete blood counts (CBCs).

FIG. 11. Effect of treatment on mean differential white blood cell (WBC) counts.

FIG. 12. Regional myocardial blood flow.

DETAILED DESCRIPTION

Figures 1A, 1B:
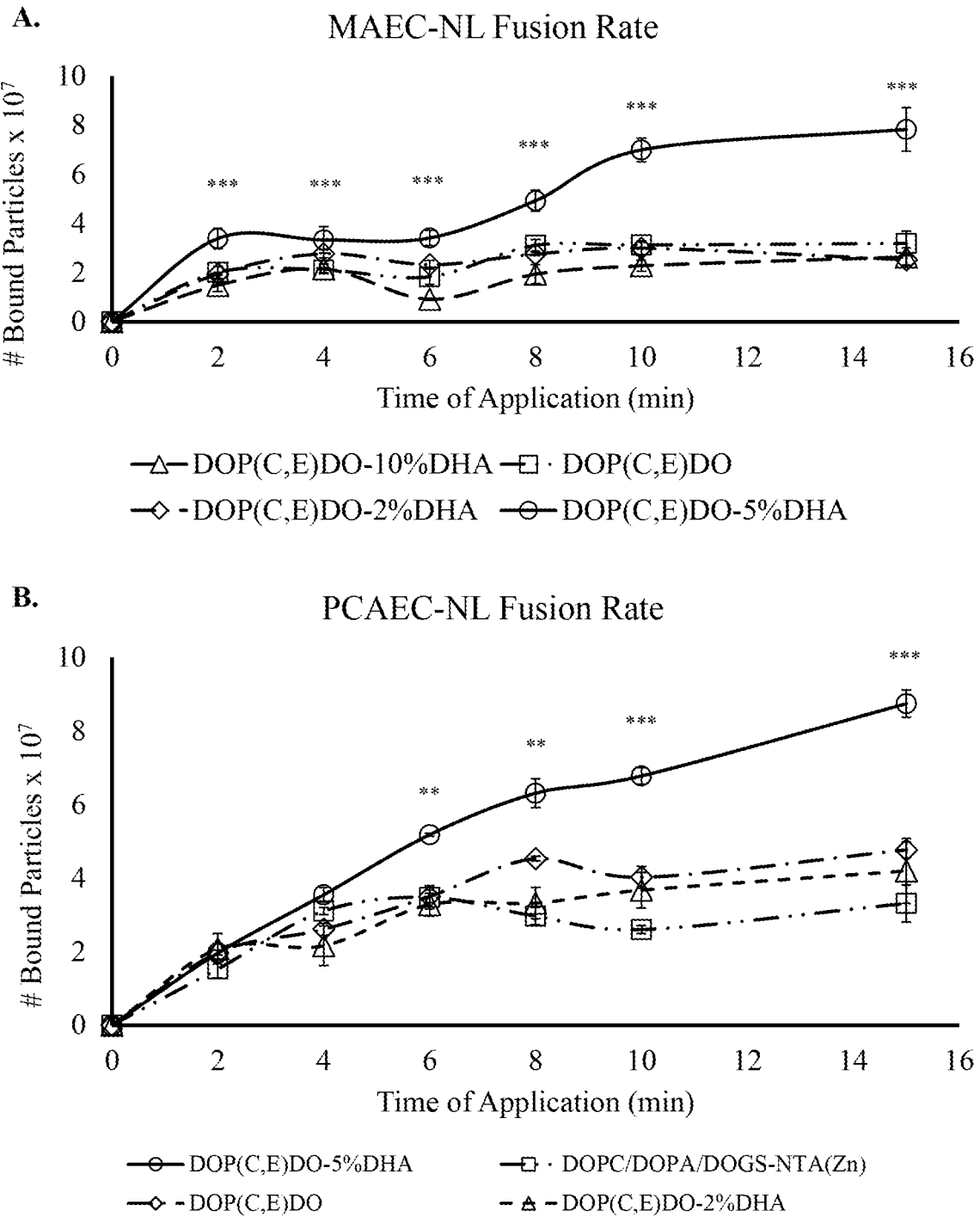
FIGS. 1A-1B. Nanoliposome (NL) fusion kinetic studies performed in vitro using mouse aortic endothelial cells (MAECs) and pig coronary arterial endothelial cells (PCAECs). A) NLs formulated with 5% DHA, and hydrated with PBS, were more effective in enhancing NL lipid incorporation into MAECs compared to NLs formulated with 0%, 2% or 10% DHA. B) NLs formulated with 5% DHA incorporated NL lipid at a faster rate into PCAECs than other NL formulations tested or with 2% DHA. DOP (C,E)DO=DOPC, DOPA, DOPE, 1.8:2.4:1 molar ratio; DOP(C,E)DO 2% DHA=DOPC, DOPA, DOPE, 1.8:2.4:1 molar ratio, with 2% DHA by weight; DOP(C,E)DO 5% DHA=DOPC, DOPA, DOPE, 1.8:2.4:1 molar ratio, with 5% DHA by weight; DOP(C,E)DO 10% DHA=DOPC, DOPA, DOPE, 1.8:2.4:1 molar ratio, with 10% DHA by weight; and CM1=DOPC, DOPA and DOGS-NTA-zinc, 1.8:2.4:1 molar ratio. Values are mean±SEM; *P<0.05 DOP(C,E)DO 5% DHA vs. all other formulations.

Coronary no-reflow is a frequent occurrence during percutaneous coronary intervention (PCI) revascularization in the setting of STEMI. Estimates of the frequency of no-reflow following revascularization range from 5% to 60%.[6, 9, 10] Patients with no-reflow tend to have worse outcomes, characterized by a large increase in congestive heart failure, cardiogenic shock, and death.[6] Patients with no-reflow that were managed with pharmaceutical therapy using distal intracoronary injections of nitroprusside, nicardipine, diltiazem, nicorandil or verapamil had improved coronary flow and better prognosis.[6, 11, 12] However, despite the better understanding by clinicians of who is at risk for no-reflow, no specific therapies have been developed and those that are used remain controversial.

Accordingly, there exists a need for medications and methods that effectively treat microvascular no-reflow phenomenon following revascularization and reperfusion to enhance tissue salvage and function, and thereby improve outcomes.

The present disclosure provides an effective strategy that can attenuate endothelial cell (EC) dysfunction, inflammation and/or the no-reflow phenomenon in the area at risk or risk region following revascularization of the affected tissue. The lipotherapy described herein is a significant advance in that it can be applied directly into the infarct related artery to target microvascular ECs at the time of intervention to reopen the clogged artery. The lipotherapy can be rapidly incorporated into the microvascular endothelium where the biologically active lipids remain to exert their effect without being washed out by the return of blood flow.

Microvascular Dysfunction and Microvascular No-Reflow Phenomenon

The present disclosure provides methods of treating microvascular dysfunctions. As used herein, the term "microvascular dysfunction" refers to a blood vessel disease in which the small blood vessels cannot provide sufficient blood flow to the tissue or organ. The microvascular dysfunction can occur in various organs and tissues. These tissues include e.g., connective tissue, muscular tissue, nervous tissue, or epithelial tissues. These organs can include e.g., lungs, heart, stomach, liver, gallbladder, pancreas, intestines, colon, rectum, kidneys, bladder, spleen, skin, brain, spinal cord, ovaries, uterus, testicles, skeletal muscles, and/or prostate, etc. In some embodiments, the organ is coronary microvascular dysfunction. As used herein, the term "coronary microvascular dysfunction" refers to a heart disease that affects the walls and inner lining of small coronary artery blood vessels, wherein the coronary artery blood vessels cannot provide sufficient blood flow to the heart muscle.

In some embodiments, the microvascular dysfunction is a disorder associated with microvascular no-reflow phenomenon. Microvascular no-reflow phenomenon occurs when tissue fails to perfuse normally despite opening of the occluded larger vessel. In some embodiments, the tissue is cardiac tissue. For example, when a short period (e.g., less than about 10, 20, 30, 40, 50, or 60 minutes) of artery occlusion occurs and then is resolved, blood flow can be distributed normally to the perfused segment. By contrast, after a prolonged occlusion (e.g., more than 60, 70, 80, 90, 100, 110 or 120 minutes), a portion of the tissue cannot regain normal perfusion despite opening of the large coronary artery. Thus, infarct expansion can still occur after the opening of the large artery. The prolonged ischemia leads to damage of the microvasculature and precludes normal perfusion. Electron microscopy studies of the damaged tissue show the presence of membrane-bound blebs protruding from the endothelial lining and swelling of the endothelial cells of the small blood vessels causing luminal obstruction. These changes are thought to be at least partially responsible for slow blood flow in the microcirculation. The present disclosure also provides methods and compositions for treating disorders or injuries associated with microvascular no-reflow phenomenon.

Lipotherapy and Nanoliposomes (NLs)

Both the intrinsic and extrinsic mechanisms can contribute to the no-reflow phenomenon: (1) intrinsic mechanisms involve endothelial dysfunction, intravascular inflammation, and endothelial swelling and disruption of the endothelial glycocalyx; (2) extrinsic mechanisms involve microvascular embolization, leukocyte plugging and myocardial edema and hemorrhage. The lipotherapy can be used to ameliorate these mechanisms, e.g., endothelial dysfunction, endothelial swelling, and leukocyte plugging in the "area at risk". As used herein, the term "lipotherapy" refers to a therapy or a treatment involving the administration of the compositions described herein (e.g., lipid compositions, phospholipids, liposomes, lipid vesicles, nanoliposomes) to a subject.

Thus, the present disclosure provides lipotherapies and compositions (e.g., lipid compositions, phospholipids, liposomes, lipid vesicles, nanoliposomes) to treat microvascular dysfunction and disorders associated with microvascular no-reflow phenomenon. In some embodiments, the composition (e.g., a lipid composition) includes phospholipids (e.g., monounsaturated phospholipids). In some embodiments, the composition includes one or more ingredients selected from the group consisting of oleic acid phospholipids, polyunsaturated fatty acids (PUFAs) and a lysosphingolipid. In some embodiments, the composition includes a combination of oleic acid phospholipids, polyunsaturated fatty acids (PUFAs) and a lysosphingolipid.

In some embodiments, these lipids can be integrated into the structure of lipid vesicles or liposomes (e.g., nanoliposomes) and form a fusogenic complex that can effectively deliver biologically active lipids into the membranes of microvascular ECs to elicit a protective effect that ameliorates the no-reflow phenomenon. In some cases, the unique property of lipotherapy NLs is that they are constructed to fuse with target ECs as soon as they come in contact with the cell membrane. The fusion rate of NLs to ECs can be increased by adding docosahexaenoic acid (DHA) as a fusogen. Increasing the fusogenicity of NLs allows the delivery of high concentrations of lipotherapy to target ECs with lower doses of lipid to achieve the desired therapeutic effect. This is advantageous for clinical treatment of no-reflow, because delivery of the bioactive lipids into the infarct related artery (IRA) need to be performed within a small-time frame prior to reperfusion during PCI following STEMI.

The compositions described herein (e.g., lipid compositions, phospholipids, liposomes, lipid vesicles, nanoliposomes, or NL lipotherapy) can be used to treat the no-reflow phenomenon during revascularization procedures to open occluded arteries in various tissues or prior to the revascularization of donor organs. In some embodiments, the compositions are in the form of fusogenic nanoliposomes or fusogenic lipid vesicles (FLVs).

In some embodiments, the compositions described herein (e.g., lipid compositions, phospholipids, liposomes, lipid vesicles, nanoliposomes, or NL lipotherapy) are injected intra-arterially during revascularization procedures to target the endothelium of microvessels in the arterial bed of the IRA. For example, in some embodiments, following myocardial infarction, the composition (e.g., lipid composition, NL lipotherapy or nanoliposomes) is administered via the infarct related coronary artery to target the endothelium of microvessels in the coronary's vascular bed or territory. The end result is the incorporation of stabilizing anti-inflammatory lipids in the membranes of ECs reducing microvascular no-reflow. In some embodiments, following stroke, the composition described herein (e.g., lipid composition, NL lipotherapy or nanoliposomes) can be administered intra-arterially to stabilize the endothelium in the microvasculature of the brain reducing the no-reflow phenomenon. In some embodiments, following the harvest of autologous tissue for reconstruction including cutaneous, skeletal muscle or myocutaneous free flaps; the composition described herein (e.g., lipid composition, NL lipotherapy or nanoliposomes) can be administered intra-arterially via the main pedicle prior to revascularization to stabilize the microvascular endothelium of flaps after transfer reducing the no-reflow phenomenon. In some embodiments, following the harvest of donor organs for allotransplantation the composition described herein (e.g., lipid composition, NL lipotherapy or nanoliposomes) can be administered intra-arterially as an adjuvant to preservation solutions prior to revascularization to stabilize the microvascular endothelium of donor tissues after transplantation reducing the no-reflow phenomenon. In some embodiments, the composition described herein (e.g., lipid composition, NL lipotherapy or nanoliposomes) can be administered as an adjuvant to cardioplegia solutions during cardiopulmonary bypass procedures to stabilize the coronary microvascular endothelium after clamp release reducing the no-reflow phenomenon in heart. In some embodiments, the vehicle or the carrier for the composition described herein (e.g., lipid composition, NL lipotherapy or nanoliposomes) is Ringer's Lactate solution, but it is not limited to Ringer's lactate solution, it can also be used with buffered solutions, saline, blood, cardioplegia and organ preservation solutions.

The present disclosure provides an intra-arterial lipotherapy that can stabilize ECs in the microvasculature by incorporating unsaturated lipids and S1P into EC membranes. This is in contrast to intra-arterial therapies using either calcium channel blockers (verapamil, diltiazem, nicardipine) or vasodilators (adenosine, nitroprusside) to treat the no-reflow phenomenon. Incorporation of unsaturated lipids changes the fluidity of EC membranes and down-modulates pro-inflammatory receptor function. Incorporation of S1P activates S1P1 receptors that reduce the shedding of EC glycocalyx, and thereby maintain endothelial barrier function. S1P levels in blood are normally high, however, S1P has a high affinity for albumin and high-density lipoproteins (HDLs),[13, 14] and thereby to protect the stability of the glycocalyx high levels of SP (100-300 nM) are needed in plasma.[13] Therapeutic administration of oral or parenteral SP would most likely bind to circulating albumin or HDL, since both are highly abundant in blood.[15] Thus, very large parenteral or oral doses of SP would be required to overcome the natural binding affinity of the lipid for these natural carriers to have a rapid therapeutic effect. Another obstacle that SP has to overcome to elicit its effect was described in crystal structure studies of the S1P1 receptor.[16] It appears that the only access that S1P has to the binding pocket of S1P1 is by entering laterally between helices I and IV within the transmembrane region of the receptor.[16] These findings suggest that SP needs to be incorporated into the cell membrane in order for it to interact with the S1P1 binding pocket. Therefore, to make SP administration a viable therapy to treat the no-reflow phenomenon following revascularization of tissues the above obstacles need to be resolved within a realistic time frame for clinical use. The methods described herein overcome these obstacles by developing a NL carrier system formulated with SP that serves two purposes: 1) It reduces the interaction of the lipid with albumin or apolipoproteins while circulating in blood; and 2) As NLs contact and fuse rapidly with ECs, effective doses of SP are incorporated into the cell membrane facilitating its access to the binding pocket of S1P1 located within the transmembrane domain of the receptor.

The present disclosure provides a composition comprising or consisting of monounsaturated lipids. In some embodiments, the compositions include fusogenic nanoliposomes formulated with oleic acid containing phospholipids hat are neutrally or negatively charged. In some embodiments, the compositions include fusogenic NLs that are formulated with polyunsaturated fatty acids (PUFAs) to promote fusion of NLs to ECs. The combination of mono-unsaturated and polyunsaturated fatty acids increases the unsaturation and fluidity of EC cell membranes, which alters receptor function. For example, in some embodiments, the lipid vesicles are delivered intra-arterially to insure contact of NLs with microvascular endothelial cells. In some embodiments, the lipid vesicles are administered intra-venous to supplement the intra-arterial infusion and enhance efficacy.

The biodistribution of the lipid vesicles is determined, at least in part, by the lipid composition, charge, and/or vesicle size thereof. For example, in some embodiments, the lipid vesicles include a lipid composition configured to increase vesicle-to-cell fusion rates. In some embodiments, a charge of the phospholipid head group can be manipulated to create dissimilar regions in the lipid layer.[43] In some embodiments, the amount of PUFA in the vesicle formulation is manipulated to create dissimilar regions in the lipid bilayer. In some embodiments, the lipid composition provides the lipid vesicle with an overall negative charge (e.g., with zeta potentials of about −60 mV to about −10 mV, about −55 mV to about −15 mV, about −45 mV to about −25 mV, about −40 mV to about −30 mV, or about −35 mV). In some embodiments, the overall negative charge of the lipid vesicles facilitates and/or promotes vesicle-to-cell fusion. Additionally or alternatively, the overall negative charge of the lipid vesicle prevents or substantially prevents the vesicles from fusing with each other.

In certain embodiments, the compositions described herein (e.g., the lipid composition, lipid vesicles, nanoliposomes, or phospholipids) includes at least one neutrally charged phospholipid and at least one negatively charged phospholipid (e.g., at physiological pH).

In some embodiment, the neutrally charged phospholipids include, but are not limited to, phosphocholines (PCs), phosphoethanolamines (PEs), or a combination thereof. In some embodiments, the negatively charged phospholipids include, but are not limited to, phosphatidic acids (PAs), phosphoserines (PSs), phosphoglycerols (PGs), or a combination thereof. For example, the composition can include a combination of PCs and PAs; a combination of PCs, PEs, and PAs; or any other suitable combination of PCs and/or PEs and PAs, PSs, and/or PGs.

In some embodiments, the composition includes one or more polyunsaturated fatty acid (PUFA), including e.g., docosahexaenoic acids (DHA), arachidonic acids (AA), eicosapentaenoic acids (EPA), or a combination thereof. Additionally or alternatively, the phospholipids can include a combination of monounsaturated and polyunsaturated phospholipids, which, in some embodiments, provides increased thermal stability. In some embodiments, the composition can include lysosphingolipids, e.g., sphingosine-1-phosphate (S1P), and its analogs FTY-720-P, KRP203, ONO-4641, GSK2018682, Ponesimod ACT-128800, SEW2871, AUY954, and VPC23019, or a combination thereof. Additionally or alternatively, S1P or its analogs can be used with charged phospholipids and unsaturated lipids.

Suitable PCs include, but are not limited to, mixed acyl PCs, such as 14:0-16:0 PC 1-myristoyl-2-palmitoyl-sn-glycero-3-phosphocholine, 14:0-18:0 PC 1-myristoyl-2-stearoyl-sn-glycero-3-phosphocholine, 16:0-14:0 PC 1-palmitoyl-2-myristoyl-sn-glycero-3-phosphocholine, 16:0-18:0 PC 1-palmitoyl-2-stearoyl-sn-glycero-3-phosphocholine, 16:0-18:1 PC 1-palmitoyl-2-oleoyl-sn-glycero-3- phosphocholine, 18:0-14:0 PC 1-stearoyl-2-myristoyl-sn-glycero-3-phosphocholine, 18:0-16:0 PC 1-stearoyl-2-palmitoyl-sn-glycero-3-phosphocholine, 18:0-18:1 PC 1-stearoyl-2-oleoyl-sn-glycero-3-phosphocholine, 18:1-14:0 PC 1-oleoyl-2-myristoyl-sn-glycero-3-phosphocholine, 18:1-16:0 PC 1-oleoyl-2-palmitoyl-sn-glycero-3-phosphocholine, and/or 18:1-18:0 PC 1-oleoyl-2-stearoyl-sn-glycero-3-phosphocholine; monounsaturated PCs, such as 14:1 (Δ9-Cis) PC 1,2-dimyristoleoyl-sn-glycero-3-phosphocholine, 16:1 (Δ9-Cis) PC 1,2-dipalmitoleoyl-sn-glycero-3-phosphocholine, 18:1 (Δ9-Cis) PC 1,2-dioleoyl-sn-glycero-3-phosphocholine (DOPC), 20:1 (Δ11-Cis) PC 1,2-dieicosenoyl-sn-glycero-3-phosphocholine, 22:1 (Δ13-Cis) PC 1,2-dierucoyl-sn-glycero-3-phosphocholine, and/or 24:1 (Δ15-Cis) PC 1,2-dinervonoyl-sn-glycero-3-phosphocholine; or a combination thereof.

Suitable PEs include, but are not limited to, mixed acyl PEs, such as, 16:0-18:1 PE 1-palmitoyl-2-oleoyl-sn-glycero-3-phosphoethanolamine and/or 18:0-18:1 PE 1-stearoyl-2-oleoyl-sn-glycero-3-phosphoethanolamine; saturated PEs, such as 12:0 PE 1,2-dilauroyl-sn-glycero-3-phosphoethanolamine, 14:0 PE 1,2-dimyristoyl-sn-glycero-3-phosphoethanolamine, 16:0 PE 1,2-dipalmitoyl-sn-glycero-3-phosphoethanolamine, and/or 18:0 PE 1,2-distearoyl-sn-glycero-3-phosphoethanolamine; monounsaturated PEs, such as 16:1 (Δ9-Cis) PE 1,2-dipalmitoleoyl-sn-glycero-3-phosphoethanolamine and/or 18:1 (49-Cis) PE 1,2-dioleoyl-sn-glycero-3-phosphoethanolamine (DOPE); or a combination thereof.

Suitable PAs include, but are not limited to, mixed acyl PAs, such as 16:0-18:1 PA 1-palmitoyl-2-oleoyl-sn-glycero-3-phosphate (POPA) (sodium salt) and/or 18:0-18:1 PA 1-stearoyl-2-oleoyl-sn-glycero-3-phosphate (SOPA) (sodium salt); monounsaturated PAs, such as 18:1 PA 1,2-dioleoyl-sn-glycero-3-phosphate (DOPA) (sodium salt); or a combination thereof.

Suitable PSs include, but are not limited to, mixed acyl PSs, such as 16:0-18:1 PS 1-palmitoyl-2-oleoyl-sn-glycero-3-phosphoserine and/or 18:0-18:1 PS 1-stearyl-2-oleoyl-sn-glycero-3-phosphoserine; monounsaturated PSs, such as 18:1 (Δ9-Cis) PS (DOPS) 1,2-dioleoyl-sn-glycero-3-phosphoserine; or a combination thereof.

Suitable PGs include, but are not limited to, mixed acyl PGs, such as 16:0-18:1 PG 1-palmitoyl-2-oleoyl-sn-glycero-3-phosphoglycerol; monounsaturated PGs, such as 18:1 (Δ9-Cis) PG 1,2-dioleoyl-sn-glycero-3-phosphoglycerol; or a combination thereof.

Suitable PUFAs include, but are not limited to, docosahexaenoic acid (DHA), arachidonic acid (AA), eicosapentaenoic acid (EPA); or a combination thereof.

Suitable lysosphingolipids include, but are not limited to, sphingosine-1-phosphate (S1P) or S1P analogs including: e.g., FTY-720-P, KRP203, ONO-4641, GSK2018682, Ponesimod ACT-128800, SEW2871, AUY954, VPC23019, or a combination thereof.

The at least one neutrally charged phospholipid and at least one negatively charged phospholipid are combined at any suitable mole ratio to provide the desired fusion rate and/or overall charge of the lipid vesicle. In some embodiments, the molar ratio of the neutrally charged phospholipids to the negatively charged phospholipids in the composition (e.g., the lipid composition, lipid vesicles, nanolipsomes, or phospholipids) can be e.g., at least or about 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, or 1:10. In some embodiments, the molar ratio is less than 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, or 1:10. In some embodiments, the molar ratio is between 5:1 and 1:1, between 4:1 and 1:1, between 3:1 and 1:1, between 2:1 and 1:1, between 1:1 and 1:2, between 1:1 and 1:3, between 1:1 and 1:4, or between 1:1 and 1:5. In some embodiments, the mole ratio of neutrally charged phospholipids to negatively charged phospholipids is between about 5:1 and about 1:1. In some embodiments, the mole ratio of neutrally charged phospholipids to negatively charged phospholipids is between 1:1 and 1.5:1, between 1:1 and 1.4:1, between 1:1 and 1.3:1, between 1:1 and 1.2:1, or between 1.1:1 and 1.2:1 (e.g., about 7:6).

In some embodiments, the composition (e.g., the lipid composition, lipid vesicles, nanoliposomes, or phospholipids) comprises PC and PE. In some embodiments, the molar ratio of the PC to the PE can be e.g., at least or about 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, or 1:10. In some embodiments, the molar ratio is less than 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, or 1:10. In some embodiments, the molar ratio is between 5:1 and 1:1, between 4:1 and 1:1, between 3:1 and 1:1, between 2:1 and 1:1, between 1:1 and 1:2, between 1:1 and 1:3, between 1:1 and 1:4, or between 1:1 and 1:5. In some embodiments, the molar ratio is between 2.5:1 and 1.5:1, between 2.3:1 and 1.7:1, between 2.2:1 and 1.8:1, or between 2.1:1 and 1.9:1 (e.g., about 2:1).

For example, in some embodiments, the lipid composition of an anionic lipid vesicle includes DOPC:DOPA:DOPE at a 3:1:2 mole ratio. In some embodiments, the lipid composition of an anionic lipid vesicle includes DOPC:DOPA:DOPE at a 1:2:1 mole ratio.

In some embodiments, the mole percentage of the neutrally charged phospholipids (e.g., PC, PE, or the combination of) among all lipids in the composition is at least or about 1%, 2%, 3%, 4%, 5%, 6%, 7%, 8%, 9%, 10%, 20%, 30%, 40%, 50%, 60%, 70%, 80%, or 90%. In some embodiments, the mole percentage is less than 1%, 2%, 3%, 4%, 5%, 6%, 7%, 8%, 9%, 10%, 20%, 30%, 40%, 50%, 60%, 70%, 80%, or 90%. In some embodiments, the mole percentage is about 20% to 90%, about 30% to 90%, about 40% to 90%, about 20% to 80%, about 20% to 85%, about 30% to 90%, about 40% to 90%, about 40% to 60%, about 45% to 55%, about 50% to 90%, about 60% to 90%, or about 70% to 90%.

In some embodiments, the mole percentage of the negatively charged phospholipids (e.g., PA, PS, PG, or the combination thereof) among all lipids in the composition is at least or about 1%, 2%, 3%, 4%, 5%, 6%, 7%, 8%, 9%, 10%, 20%, 30%, 40%, or 45%. In some embodiments, the mole percentage is less than 1%, 2%, 3%, 4%, 5%, 6%, 7%, 8%, 9%, 10%, 20%, 30%, 40%, or 50%. In some embodiments, the mole percentage is about 5% to 50%, about 5% to 40%, about 5% to 30%, about 5% to 20%, about 10% to 50%, about 10% to 40%, about 10% to 40%, about 10% to 25%, or about 10% to 20%.

One or more PUFAs can be combined with at least one neutral and one negatively charged lipid at any suitable mole ratio to provide the desired fusion rate and/or overall charge of the NL. In some embodiments, the mole ratio of the negatively charged phospholipids to PUFA can be e.g., at least or about 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, or 1:10. In some embodiments, the molar ratio is less than 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, or 1:10. In some embodiments, the molar ratio is between 5:1 and 1:1, between 4:1 and 1:1, between 3:1 and 1:1, between 2:1 and 1:1, between 1:1 and 1:2, between 1:1 and 1:3, between 1:1 and 1:4, or between 1:1 and 1:5.

In some embodiments, the mole ratio of the phospholipids to PUFA can be e.g., at least or about 20:1, 19:1, 18:1, 17:1, 16:1, 15:1, 14:1, 13:1, 12:1, 11:1, 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, or 1:10. In some embodiments, the molar ratio is less than 20:1, 19:1, 18:1, 17:1, 16:1, 15:1, 14:1, 13:1, 12:1, 11:1, 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, or 1:10. In some embodiments, the molar ratio is between 20:1 and 1:1, between 15:1 and 5:1, between 12:1 and 8:1, between 11:1 and 9:1 (e.g., about 10:1).

In some embodiments, the weight percentage of PUFA (e.g., DHA) among all lipids in the composition is at least or about 1%, 2%, 3%, 4%, 5%, 6%, 7%, 8%, 9%, or 10%. In some embodiments, the weight percentage is less than 1%, 2%, 3%, 4%, 5%, 6%, 7%, 8%, 9%, or 10%. In some embodiments, the weight percentage is about 3% to 7%, about 4% to 6%, or about 5%. In some embodiments, the PUFA can increase the fusion rate (e.g., as determined by the number of lipid vesicles that are fused to cells within a period of time) by about or at least 10%, 20%, 30%, 40%, 50%, 60%, 70%, 80%, 90%, 1 fold, 2 fold, 3 fold, or 5 fold.

For example, in some embodiments, the lipid composition of an anionic lipid vesicle includes DOPC:DOPA:DOPE:DHA at a 4:1:4:1 mole ratio. In some embodiments, the lipid composition of an anionic lipid vesicle includes DOPC:DOPA:DOPE:DHA at a 3:4:2:1 mole ratio.

One or more lysosphingolipids can be combined with at least one neutral, one negatively charged phospholipids at any suitable mole ratio to provide the desired fusion rate and/or overall charge of the lipid vesicle. In some embodiments, the mole ratio of the phospholipids to lysosphingolipid is at least or about 200:1, 190:1, 180:1, 170:1, 160:1, 150:1, 140:1, 130:1, 120:1, 110:1, 100:1, 90:1, 80:1, 70:1, 60:1, 50:1, 40:1, 30:1, 20:1, or 10:1. In some embodiments, the molar ratio is less than 200:1, 190:1, 180:1, 170:1, 160:1, 150:1, 140:1, 130:1, 120:1, 110:1, 100:1, 90:1, 80:1, 70:1, 60:1, 50:1, 40:1, 30:1, 20:1, or 10:1. In some embodiments, the molar ratio is between 200:1 and 10:1, between 150:1 and 50:1, between 140:1 and 60:1, between 130:1 and 70:1, between 120:1 and 80:1, or between 110:1 and 100:1 (e.g., about 100:1).

In some embodiments, the weight percentage of the lysosphingolipid (e.g., S1P, its analog, or the combination thereof) among all lipids in the composition is at least or about 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, or 10%. In some embodiments, the weight percentage is less than 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, or 10%. In some embodiments, the weight percentage is about 0.1% to 1%, about 0.2% to 0.9%, about 0.3% to 0.8%, about 0.4% to 0.7%, about 0.4% to 6%, or about 0.5%. In some embodiments, the lysosphingolipid can increase the fusion rate (e.g., as determined by the number of lipid vesicles that are fused to cells within a period of time) by about or at least 10%, 20%, 30%, 40%, 50%, 60%, 70%, 80%, 90%, 1 fold, 2 fold, or 3 fold.

For example, in some embodiments, the lipid composition of an anionic lipid vesicle includes DOPC:DOPA:DOPE:DHA:S1P at a 4:1:3.8:1:0.2 mole ratio. In some embodiments, the lipid composition of an anionic lipid vesicle includes DOPC:DOPA:DOPE:DHA:S1P at a 3:4:1.8:1:0.08 mole ratio.

Methods of making lipid vesicles (e.g., liposomes, nanoliposomes) are generally known in the art, including, liquid hydration or solvent spherule preparation for making multi-laminar vesicles (having series of concentric bi-layer of lipid), sanitation, French press, solvent injection, detergent removal, reverse phase evaporation, calcium induced fusion, microfluidization or freeze-thaw methods to prepare unilaminar vesicles (having a single layer of lipids), etc. These methods are described e.g., in U.S. Pat. Nos. 7,220,538, 6,217,899; US Patent Publication No. 20100021531, Lichtenberg et al., Methods Biochem Anal. 33:337-462, 1988; and G. Gregoriadis: "Liposome Technology Liposome Preparation and Related Techniques," 2nd edition, Vol. I-III, CRC Press. Liposomes for pharmaceutical use have been disclosed in Mozafari, M., Liposomes, Methods and Protocols Vol. 1, Chapter 2, V. Wessing Ed. 2010, Humana Press), each of which is incorporated herein by reference in the entirety.

In some embodiments, the lipid soluble components are mixed in a chloroform solution. The chloroform is evaporated in vacuo. The lipid mixture is hydrated with a hydrating solution. The lipid mixture in hydrating solution is warmed and vortexed to suspend the lipid mixture. The suspension is sonicated, centrifuged, and extruded through various size porous membranes to form liposomes with desired size (e.g., nanoliposomes).

In some embodiments, the present disclosure provides a composition comprising a plurality of nanoliposomes. These nanoliposomes can have a diameter or an average diameter of about or at least 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 350, 400, 450, 500 nm. In some embodiments, the diameter or the average diameter is less than 50, 60, 70, 80, 90, 100, 110, 120, 130, 140, 150, 160, 170, 180, 190, 200, 210, 220, 230, 240, 250, 260, 270, 280, 290, 300, 350, 400, 450, 500 nm. In some embodiments, the diameter or the average diameter is from about 10 nm to about 500 nm, from about 10 nm to about 400 nm, from about 10 nm to about 300 nm, from about 10 nm to about 200 nm, from about 10 nm to about 150 nm, from about 10 nm to about 100 nm, from about 50 nm to about 500 nm, from about 50 nm to about 400 nm, from about 50 nm to about 300 nm, from about 50 nm to about 250 nm, from about 50 nm to about 200 nm, from about 50 nm to about 1500 nm, or from about 50 nm to about 100 nm.

In some embodiments, the lipid vesicles have a diameter of up to 250 nm. In some embodiments, the lipid vesicles have a diameter of up to 150 nm. More specifically, in some embodiments, the lipid vesicles have a diameter of between 50 nm and 250 nm or between 50 nm and 150 nm. In some embodiments, when administered to a subject intra-arterially, this combination of formulation, charge, and size targets the microvascular endothelium and fuses delivering therapeutic lipids.

Methods of Treatment

The methods described herein include methods for the treatment of disorders associated with microvascular dysfunction, disorders or injuries associated with microvascular no-reflow phenomenon in a subject. In some embodiments, the methods described herein can increase blood flow during revascularization, treat microvascular no-reflow phenomenon (e.g., in tissues affected by the revascularization of a blocked artery), reduce an anatomic zone of no-reflow, stabilize and maintain microvascular barrier function, reduce microvascular dysfunction, or reduce infarct size during revascularization.

Generally, the methods include administering a therapeutically effective amount of the composition described herein (e.g., lipid composition, phospholipids, lipid vesicles, liposomes, NL lipotherapy, or nanoliposomes), to a subject who is in need of, or who has been determined or identified to be in need of, such treatment. In some embodiments, the subject has been determined to have or likely to have microvascular dysfunction, disorders or injuries associated with microvascular no-reflow phenomenon, or in need of coronary intervention.

As used herein, the terms "subject" and "patient" are used interchangeably throughout the specification and describe an animal, preferably a human or non-human mammal, to whom treatment according to the methods of the present invention is provided. Veterinary and non-veterinary applications are contemplated by the present invention. Human patients can be adult humans or juvenile humans (e.g., humans below the age of 18 years old). In addition to humans, patients include but are not limited to mice, rats, hamsters, guinea-pigs, rabbits, ferrets, cats, dogs, and primates. Included are, for example, non-human primates (e.g., monkey, chimpanzee, gorilla, and the like), rodents (e.g., rats, mice, gerbils, hamsters, ferrets, rabbits), lagomorphs, swine (e.g., pig, miniature pig), equine, canine, feline, bovine, and other domestic, farm, and zoo animals.

As used herein, to "treat" means to ameliorate at least one symptom of the disorder associated with microvascular dysfunction (e.g., disorders or injuries associated with microvascular no-reflow phenomenon) or other disorders described herein. Often, the treatment results in an increase of blood flow in the blood vessels (e.g., microvascular structure or networks). Thus, a treatment can result in a reduction in ischemia, and/or a reduction of infarct size.

In some embodiments, the composition described herein (e.g., lipid composition, phospholipids, lipid vesicles, liposomes, NL lipotherapy, or nanoliposomes) is designed for intravascular delivery during percutaneous vascular interventions such as PCI. Additionally, the compositions described herein can be used to treat microvascular no-reflow in tissues subjected to ischemia and revascularization following surgical interventions including: e.g., free flap transfer, organ transplantation, and during cardioplegia in cardiopulmonary bypass. As the composition described herein (e.g., lipid composition, phospholipids, lipid vesicles, liposomes, NL lipotherapy, or nanoliposomes), described herein comes in contact with ECs in microvascular vessels, biologically active lipids are incorporated into ECs to stabilize the cell membrane microenvironment following revascularization. This includes the stabilization of the surface glycocalyx layer of ECs that is a component of the blood-to-tissue permeability barrier.

The stabilizing effects on ECs by the lipotherapy described herein are produced by two components: 1) Incorporating mono- and poly-unsaturated NL lipids increases the level of cell membrane unsaturation and fluidity, which appear to downmodulate pro-inflammatory receptor function, and thus, decreases EC activation; and/or 2) Incorporating the lysosphingolipid sphingosine-1-phosphate (S1P) into EC membrane bilayer via NL delivery, increases the lipid's bioavailability to binding pocket of the sphingosine-1-phosphate receptor 1 (S1P1) located in the transmembrane domain, which when activated, reduces the shedding of the EC glycocalyx.

Administering the composition described herein (e.g., lipid composition, phospholipids, lipid vesicles, liposomes, NL lipotherapy, or nanoliposomes) during revascularization of affected tissues reduces EC activation, microvascular dysfunction and ameliorates the "no-reflow" phenomenon enhancing tissue salvage. Additionally, the composition described herein (e.g., lipid composition, phospholipids, lipid vesicles, liposomes, NL lipotherapy, or nanoliposomes) can interact with circulating leukocytes in affected tissues and incorporate biologically active lipids into their membranes to attenuate leukocyte release of pro-inflammatory factors, thereby reducing EC activation and edema, two important contributors to the "no-reflow" phenomenon.

Administering the composition described herein (e.g., lipid composition, phospholipids, lipid vesicles, liposomes, NL lipotherapy, or nanoliposomes) following stroke can potentially reduce EC activation, microvascular dysfunction and ameliorate the "no-reflow" phenomenon enhancing neural tissue salvage. Additionally, the composition described herein (e.g., lipid composition, phospholipids, lipid vesicles, liposomes, NL lipotherapy, or nanoliposomes) can interact with circulating leukocytes in affected brain tissues and incorporate biologically active lipids into their membranes to attenuate leukocyte release of pro-inflammatory factors, thereby reducing EC activation and edema.

In some embodiments, the methods described herein can be used in combination with some other medications, e.g., verapamil, nitroprusside, and/or nicorandil. In some cases, these medications are administered into the infarct-related artery (IRA), and can be beneficial in restoring microvascular flow.

Methods described herein can also be used to treat or attenuate ischemia and/or reperfusion injury. Ischemia is a restriction in blood supply to tissues, causing a shortage of oxygen that is needed for cellular metabolism (to keep tissue alive). Ischemia is generally caused by problems with blood vessels, with resultant damage to or dysfunction of tissue. In some cases, it can result from congestion (such as vasoconstriction, thrombosis or embolism). Ischemia comprises not only insufficiency of oxygen, but also reduced availability of nutrients and inadequate removal of metabolic wastes. Reperfusion injury refers to the tissue damage caused when blood supply returns to tissue after a period of ischemia or lack of oxygen (anoxia or hypoxia). The absence of oxygen and nutrients from blood during the ischemic period creates a condition in which the restoration of circulation results in inflammation and oxidative damage through the induction of oxidative stress rather than (or along with) restoration of normal function.

Ischemia and reperfusion injury can occur in various tissues, e.g., connective tissue, muscular tissue, nervous tissue, or epithelial tissues, or various organs, e.g., lungs, heart, stomach, liver, gallbladder, pancreas, intestines, colon, rectum, kidneys, bladder, spleen, skin, brain, spinal cord, ovaries, uterus, testicles, skeletal muscles, and/or prostate, etc. These injuries or diseases include, but are not limited to, ischemic colitis, mesenteric ischemia, brain ischemia, stroke, acute limb ischemia, cyanosis and gangrene etc. The described method can be also employed to treat ischemia injury in these organs/tissues. For these treatments, the compositions described herein can be injected to the organ tissue or injected into the blood vessel (e.g., around the affected tissue and/or organs).

Reperfusion injury is the tissue damage by blood supply when blood returns to the tissue after a period of ischemia or lack of oxygen. The absence of oxygen and nutrients during the ischemic period results in inflammation and oxidative damage when blood flow is restored. The inflammatory response further leads to the reperfusion injury in the tissue. Therefore, in some embodiments, the treatment also involves administering immune suppressors to the patient. The immune suppressors can be, e.g., administrated separately, but as a concurrent treatment with the composition described herein (e.g., lipid composition, phospholipids, lipid vesicles, liposomes, NL lipotherapy, or nanoliposomes).

In some embodiments, the lipid vesicles (e.g., liposomes or nanoliposomes) can provide a high fusion kinetic. In some embodiments, at least or about 10 million, 20 million, 30 million, 40 million, 50 million, 60 million, 70 million, 80 million, 90 million or 100 million lipid vesicles (e.g., liposomes or nanoliposomes) are bound and/or are fused to cell membrane of ECs within 15 minutes under appropriate conditions (e.g., as tested on mouse aortic ECs (MAECs) or pig coronary arterial ECs (PCAECs)). In some embodiments, at least or about 1%, 2%, 3%, 4%, 5%, 6%, 7%, 8%, 9%, or 10% of the lipid vesicles are bound and/or fused to cell membrane of ECs within 15 minutes within a short period of time (e.g., 15 minutes, or 1 hour under the conditions described herein).

The methods described herein can also reduce inflammatory response, inhibit the activation of cells (e.g., ECs or immune cells), inhibit immune response, or reduce the activity of immune cells (e.g., T cells, CD8+ T cells, CD4+ T cells, macrophages, antigen presenting cells) by at least 10%, 20%, 30%, 40%, 50%, 60%, 70%, 80%, or 90%. In some embodiments, the compositions described herein can inhibit production or activity of proinflammatory cytokines or cytokines. In some embodiments, the compositions described herein can inhibit the expression or secretion of tumor necrosis factor (TNF) by about or at least 10%, 20%, 30%, 40%, 50%, 60%, 70%, 80%, or 90% (e.g., as determined by a supernatant TNF assay). In some embodiments, the compositions described herein can inhibit the expression or activity of ICAM-1 by about or at least 10%, 20%, 30%, 40%, 50%, 60%, 70%, 80%, or 90% (e.g., as determined by an ICAM-1 expression assay).

In some embodiments, the methods described herein can reduce infarct size by about or at least 10%, 20%, 30%, 40%, 50%, 60%, 70%, 80%, or 90% (e.g., as compared to the infarct size in a subject without receiving the treatment of the compositions described herein).

In some embodiments, the compositions described herein can be administered before, during, or after ischemia occurs. In some embodiments, the compositions described herein can be administered before, during, or after reperfusion. In some embodiments, the compositions described herein can be administered to a subject more than 10, 20, 30, 40, 50, 60, 70, 80, 90, 100, 110, 120 minutes, or more than 3, 4, 5, 6, 7, 8, 9, 10, 11, 12, 13, 14, 15, 16, 17, 18, or 24 hours after ischemia has occurred. In some embodiments, the compositions described herein can be administered to a subject within 60, 70, 80, 90, 100, 110, 120 minutes, or 3, 4, 5, 6, 7, 8, 9, 10, 11, 12, 13, 14, 15, 16, 17, 18, or 24 hours after ischemia has occurred. In some embodiments, the compositions described herein can be administered to a subject within 60, 70, 80, 90, 100, 110, 120 minutes, or 3, 4, 5, 6, 7, 8, 9, 10, 11, 12, 13, 14, 15, 16, 17, 18, or 24 hours before reperfusion or the restore of the blood flow.

In some embodiments, the composition described herein can increase blood flow by about or at least 10%, 20%, 30%, 40%, 50%, 60%, 70%, 80%, 90%, 100%, 2 fold, 3 fold, 4 fold or 5 fold (e.g., as compared to a subject without receiving the composition). In some embodiments, the blood flow refers to myocardial blood flow.

In some embodiments, the methods described herein can reduce microvascular no-reflow, for example, as determined by one or more serum biomarkers of microvascular no-reflow. In some embodiments, the biomarker is the serum heart-type fatty acid binding protein (hFABP) level. In some embodiments, the methods described herein can reduce serum hFABP levels by about or at least 10%, 20%, 30%, 40%, 50%, 60%, 70%, 80%, or 90%.

In some embodiments, the compositions described herein are administered to a subject in connection with percutaneous coronary intervention (PCI), for example, before, during, or after PCI.

In some embodiments, a calcium channel blockers (e.g., verapamil, diltiazem, nicardipine), a vasodilator (e.g., adenosine, nitroprusside), an anti-thrombotic agent, and/or a platelet aggregation inhibitor can also be administered to the subject.

The ischemia-reperfusion injury is a very important problem during organ transplantation. Much damage in organ transplantation appears to be induced by reperfusion injury. Organs used for transplantation often undergoes lengthy periods of cold ischemic storage after devascularization and cold perfusion, resulting in an increased susceptibility to damage upon reperfusion. Methods described herein can be used to control ischemia/reperfusion damage for transplanted organs. In some cases, the transplanted organ can be any organ as described herein, e.g., a heart, a lung, a kidney, or a liver, etc. In some embodiments, an effective amount the compositions described herein are injected into the blood vessels (e.g., arteries) of the transplanted organ. In some instances, the injection is performed before the organ is retrieved from the donor. In some instances, the injection is performed at some time point after organ is retrieved, but before it is transplanted. In some instances, the injection is performed after the organ is transplanted into the recipient. In some instances, injections are performed before organ retrieval, after harvesting of the organ, and then again after implantation into the recipient. In some instances, the injection is performed during the transplantation surgery. In some embodiments, the transplanted organ is preserved in a solution containing an effective amount of the compositions described herein.

Dosage

As used herein, an "effective amount" is an amount sufficient to effect beneficial or desired results. For example, a therapeutic amount is one that achieves the desired therapeutic effect. This amount can be the same or different from a prophylactically effective amount, which is an amount necessary to prevent onset of disease or disease symptoms. An effective amount can be administered in one or more administrations, applications or dosages. A therapeutically effective amount of a composition (i.e., an effective dosage) depends on the compositions selected. The compositions can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the compositions described herein can include a single treatment or a series of treatments.

Dosage, toxicity and therapeutic efficacy of the composition described herein (e.g., lipid composition, phospholipids, lipid vesicles, liposomes, NL lipotherapy, or nanoliposomes) can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. The compositions or agents which exhibit high therapeutic indices are preferred. While the compositions or agents that exhibit toxic side effects may be used, care should be taken to design a delivery system that targets such composition (e.g., lipid composition, phospholipids, lipid vesicles, liposomes, NL lipotherapy, or nanoliposomes) to the site of affected tissue in order to minimize potential damage to unaffected cells and, thereby, reduce side effects.

The data obtained from cell culture assays and animal studies can be used in formulating a range of dosage for use in humans. The dosage of such composition (e.g., lipid composition, phospholipids, lipid vesicles, liposomes, NL lipotherapy, or nanoliposomes) lies preferably within a range of circulating concentrations that include the ED50 with little or no toxicity. The dosage may vary within this range depending upon the dosage form employed and the route of administration utilized. For any composition or agent used in the method of the invention, the therapeutically effective dose can be estimated initially from cell culture assays. A dose may be formulated in animal models to achieve a circulating plasma concentration range that includes the IC50 (i.e., the concentration of the test agent which achieves a half-maximal inhibition of symptoms) as determined in cell culture. Such information can be used to more accurately determine useful doses in humans. Levels in plasma may be measured, for example, by high performance liquid chromatography.

In the treatment of the disorders or symptoms as described herein, an appropriate dosage level will generally be about 1 to 500 mg of the composition (e.g., lipid composition, phospholipids, lipid vesicles, liposomes, NL lipotherapy, or nanoliposomes) per administration, and can be administered in single or multiple doses. In some embodiments, the dosage level will be about 1 to about 400 mg per administration; about 1 to 300 mg per administration; about 1 to 200 mg per administration; about 5 to 200 mg per administration; about 10 to 200 mg per administration; or about 50 to 200 mg per administration. This dosing regimen can be adjusted to provide the optimal therapeutic response.

It is understood, however, that the specific dose level for any particular patient will depend upon a variety of factors. Such factors include the age, body weight, general health, sex, and diet of the patient. Other factors include the time and route of administration, rate of excretion, drug combination, and the type and severity of the particular disease undergoing therapy.

Pharmaceutical Compositions and Methods of Administration

The methods described herein include the use of pharmaceutical compositions comprising lipids, phospholipids, lipid vesicles, liposomes, NL lipotherapy, or nanoliposomes described herein as an active ingredient(s).

Pharmaceutical compositions typically include a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration.

In some embodiments, the carrier for the composition described herein is Ringer's Lactate solution, buffered solutions, saline, blood, cardioplegia or organ preservation solutions, etc. The Ringer's Lactate solution comprise sodium chloride, sodium lactate, potassium chloride, calcium chloride, and water.

In some embodiments, one liter of Ringer's lactate solution contains:
- 130-131 mEq of sodium ion (130 mmol $L^{-1}$),
- 109-111q of chloride ion (109 mmol $L^{-1}$),
- 28-29 Eq of lactate ion (28 mmol $L^{-1}$),
- 4-5 mEq of potassium ion (4 mmol $L^{-1}$), and
- 2-3 mEq of calcium ion=(1.5 mmol $L^{-1}$).

In some embodiments, the compositions described herein can be included in compositions that are designed for use in organ, tissue, or cell transplantation. The composition may include lipid composition, phospholipids, lipid vesicles, liposomes, NL lipotherapy, or nanoliposomes as described herein, and a liquid that is suitable for administration to patients or for maintaining organs, tissues or cells ex vivo. In general, the liquid will be an aqueous solution. Examples of solutions include Phosphate Buffered Saline (PBS), Celsior™ solution, Perfadex™ solution, Collins solution, citrate solution, tissue culture media (e.g., Dulbecco's Modified Eagle's Medium (DMEM)), the Histidine-tryptophan-ketoglutarate (HTK) solution, and the University of Wisconsin (UW) solution (Oxford Textbook of Surgery, Morris and Malt, Eds., Oxford University Press, 1994).

The University of Wisconsin cold storage solution is considered the current golden standard solution for organ transplantation. It includes the following: 100 mM potassium lactobionate, 25 mM $KH_2PO_4$, 5 mM $MgSO_4$, 30 mM raffinose, 5 mM adenosine, 3 mM glutathione, 1 mM allopurinol, and 50 g/L hydroxyethyl starch. The lipids, phospholipids, lipid vesicles, liposomes, NL lipotherapy, or nanoliposomes described herein can be added to these liquids for organ, tissue and cell preservation.

In some embodiments, the composition is at a physiological pH, e.g., the pH of blood (e.g., about 7 to about 7.5, or about 7.34 to about 7.45).

In some embodiments, supplementary active agents can also be incorporated into the compositions, e.g., nitroprusside, nicardipine, diltiazem, nicorandil or verapamil.

Pharmaceutical compositions are typically formulated to be compatible with its intended route of administration. Examples of routes of administration include parenteral, e.g., intravenous, intradermal, subcutaneous, oral (e.g., inhalation), transdermal (topical), transmucosal, and rectal administration.

Methods of formulating suitable pharmaceutical compositions are known in the art, see, e.g., *Remington: The Science and Practice of Pharmacy,* 21st ed., 2005; and the books in the series *Drugs and the Pharmaceutical Sciences: a Series of Textbooks and Monographs* (Dekker, NY). For example, solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating the compositions in the required amount in an appropriate solvent with one or a combination of ingredients enumerated above, as required, followed by filtered sterilization. Generally, dispersions are prepared by incorporating the compositions into a sterile vehicle, which contains a basic dispersion medium and the required other ingredients from those enumerated above.

For administration by inhalation, the compositions can be delivered in the form of an aerosol spray from a pressured container or dispenser that contains a suitable propellant, e.g., a gas such as carbon dioxide, or a nebulizer. Such methods include those described in U.S. Pat. No. 6,468,798.

In some embodiments, the compositions are prepared with carriers that will protect the active ingredients against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques, or obtained commercially.

The pharmaceutical compositions can be included in a container, pack, or dispenser together with instructions for administration.

EXAMPLES

The invention is further described in the following examples, which do not limit the scope of the invention described in the claims.

Example 1. In Vitro Studies Demonstrate that DHA Increases NL-to-Cell Fusion To determine whether NL lipotherapy is a viable option for the rapid delivery of bioactive lipids to ECs, in vitro fusion studies were performed. Fusion kinetic studies of NLs-labeled with rhodamine were performed using mouse aortic ECs (MAECs) and pig coronary arterial ECs (PCAECs). Cells were cultured in 96-well plates and were incubated with equal amounts of rhodamine-labeled NLs for different time durations. After incubation, the rhodamine-labeled NLs were washed out and the fluorescence was measured using a microplate reader. Fluorescence levels were converted to number of rhodamine-labeled NLs fused using a rhodamine-lipid standard calibration curve.

The Effect of DHA Content in NL-to-EC Fusion Kinetics

To determine whether NL lipotherapy is a viable option for the delivery of lipids into ECs during percutaneous vascular interventions, NL lipotherapy fusion kinetic studies were performed using MAECs and PCAECs. Plated cells were incubated for 0, 2, 4, 6, 8, 10, and 15 min with NLs formulated with DOPC, DOPE, DOPA, and different concentrations of DHA (0, 2, 5 or 10%). Also, PCAECs were incubated with a different fusogenic NL formulation containing oleic acids (DOPC, DOPA and DOGS-NTA), but no DHA. NLs were labeled with rhodamine for fluorescent detection. Experimental results showed that the rate of NL lipid incorporation into MAECs quantified as the number of NLs bound to cells over time was greatest in the NL formulation containing 5% DHA (FIG. 1A). Similarly, the rate of NL lipid incorporation into PCAECs was greatest when the NL formulation contained 5% DHA (FIG. 1B). These results suggest that adding 5% DHA to the NL formulation enhances the rate of fusion of vesicles to ECs. In addition, these results suggest that NL lipotherapy formulated with 5% DHA incorporates at a faster rate a significant amount of lipid into ECs within 15 min of administration, a time that is reasonable for the potential use of NL lipotherapy to treat the vascular endothelium to reduce the no-reflow phenomenon during revascularization of occluded arteries using PCIs.

Effects of DHA and S1P Content in NL-to-EC Fusion Kinetics

To determine whether NL lipotherapy is a viable option for the delivery of lipids to ECs during percutaneous coronary intervention (PCI), preliminary fusion kinetic studies of NLs formulated with DOPC, DOPE, DOPA, and different amounts of DHA and S1P, were performed using PCAECs and MAECs. NLs were labeled with rhodamine for fluorescent detection. Cells were incubated for 0, 2, 4, 6, 8, 10, and 15 min with NLs formulated with DOPC, DOPE, DOPA only or DOPC, DOPE, DOPA and one of the following combinations of DHA and S1P: 5% DHA only, 0.5% SP only or 5% DHA and 0.5% S1P combined. Experimental results showed that the rate of NL lipid incorporation into PCAECs quantified as the number of rhodamine vesicles bound to cells over time was greatest in the NL formulation containing 5% DHA and 0.5% SP (FIG. 2A).

Similarly, the rate of NL lipid incorporation into MAECs was greatest when the NL formulation contained 5% DHA and 0.5% S1P (FIG. 2B). These results suggest that adding 0.5% SP to the NL formulation containing 5% DHA further enhances the rate of fusion of vesicles to PCAECs and MAECs. In addition, these results suggest that NL lipotherapy formulated with a combination of 5% DHA and 0.5% SP incorporates at a faster rate the greatest amount of lipid into ECs within 15 min of administration, a time that is reasonable for the potential use of NL lipotherapy to treat the vascular endothelium to reduce the no-reflow phenomenon during revascularization of occluded arteries using PCI.

Example 2. NL Lipotherapy Reduces Pro-Inflammatory Response of Macrophages and ECs To determine whether NL lipotherapy reduces the inflammatory response of macrophages and ECs, in vitro studies were performed by pre-treating cells with NL lipotherapy and quantifying their response to either lipopolysaccharide (LPS) or swine plastic contact activated plasma. LPS response studies were performed using RAW 264.7 cells (mouse macrophages) and activated plasma response studies were performed using MCAECs. Both cell types were pre-treated with NL lipotherapy. After pre-treatment, RAW cells were challenged with LPS overnight, and MCAECs were incubated with plastic contact activated plasma. RAW cell supernatant was collected and analyzed for TNF, and MCAEC cell activation was quantified by measuring intercellular adhesion molecule-1 (ICAM-1) expression.

NL Lipotherapy Reduces TNF Production in Macrophages

Figure 3:
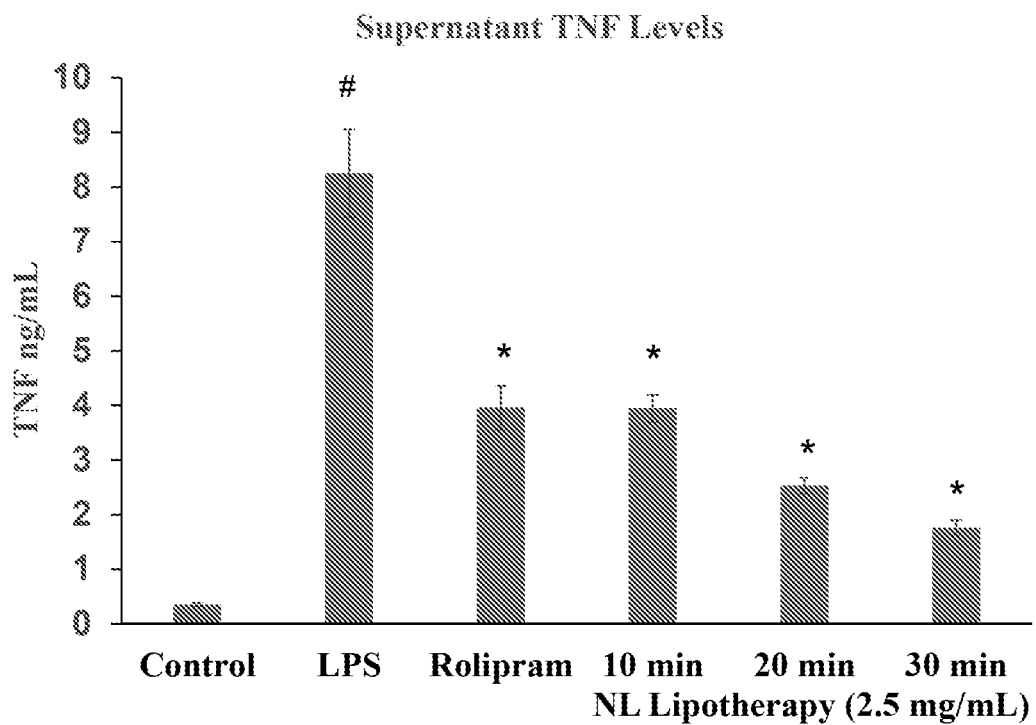
FIG. 3. Nanoliposome (NL) lipotherapy reduces RAW cell (mouse macrophage) activation when treated with lipopolysaccharide (LPS). The negative control group (−) received no treatment, and the positive control group (+) was treated with LPS. Treated RAW cell groups, received NLs formulated with DOPC, DOPA, DOPE, 1.8:2.4:1 molar ratio, with 5% DHA and 0.5% S1P by weight, hydrated with PBS, and incubated for 5, 15, and 30 minutes followed by LPS (100 ng/mL) treatment for 24 hours at 37° C. These results show that the application of NL lipotherapy prior to LPS stimulation reduces the TNF-α production significantly, and considerable reduction can be achieved with 5 minutes of treatment application. Values are mean±SEM; *P<0.05 vs. (+) control or NL FIG. 4. Nanoliposome (NL) lipotherapy reduces ICAM-1 expression of mouse coronary artery endothelial cells (MCAECs) following incubation with plastic contact activated plasma (PCAP) diluted with media at a 1:4 ratio. Cells were divided into six treatment groups: Group 1 cells were the negative control (−) and received no treatment; Group 2 cells were the positive control (+) and were incubated with PCAP; Groups 3-5 were pretreated for 20 min with 2.5, 5.0 or 10.0 mg/mL of NL lipotherapy formulated with DOPC, DOPA, DOPE, 1.8:2.4:1 molar ratio, with 5% DHA and 0.5% S1P by weight, hydrated with Ringer's lactate, and incubated with PCAP. Group 6 cells were treated with horse radish peroxidase-labeled antibodies as a background control. After PCAP treatment cells were washed and incubated in media for 1 h prior to quantifying ICAM-1 expression. These results show that NL lipotherapy prior to PCAP incubation reduced ICAM-1 expression significantly. Values are mean±SEM; *P<0.027 vs. (+) control; P<0.001 vs. all groups.

To determine whether NL lipotherapy reduces the inflammatory response of macrophages, in vitro studies were performed on RAW cells cultured in 24-well plates. RAW cells were pre-treated with 2.5 mg/mL of NL lipid formulated with DOPC, DOPA, DOPE, 1.8:2.4:1 molar ratio, with 5% DHA and 0.5% S1P by weight, and their response to lipopolysaccharide (LPS) exposure (100 ng/mL) for 24 h at 37° C. was quantified by measuring supernatant levels of TNF. Five groups of RAW cells were studied: in Group 1, cells did not receive treatment (negative control); in Group 2, cells were treated with LPS (positive control); in Group 3, cells were treated with of rolipram (10 µM) and exposed to LPS; in Groups 4-6, cells were pre-treated with NL lipotherapy for 10, 20 and 30 min and expose to LPS. TNF levels were quantified using a mouse TNF ELISA kit (Cat. No. KMC3012, ThermoFisher Scientific, Grand Island, N.Y.). Experimental results demonstrated that RAW cells treated with NL lipotherapy produced less TNF than untreated cells (FIG. 3). Also, these findings indicated that a 10-min incubation period with NL lipotherapy elicited a similar TNF attenuation-response as cells treated with rolipram (a TNF inhibitor). In summary, NL lipotherapy attenuates the activation of RAW cells exposed to LPS. A 10-min incubation period of NL lipotherapy appears to be sufficient to attenuate the pro-inflammatory response of macrophages. The implication of these studies is that the protective anti-inflammatory effect observed in vitro may also occur in vivo when the lipotherapy is administered to the microvascular bed of the infarct related artery during revascularization procedures. If true, the therapy may attenuate the macrophage contribution to reperfusion injury and the no-reflow phenomenon.

NL Lipotherapy Reduces ICAM-1 Expression in ECs

Figure 4:
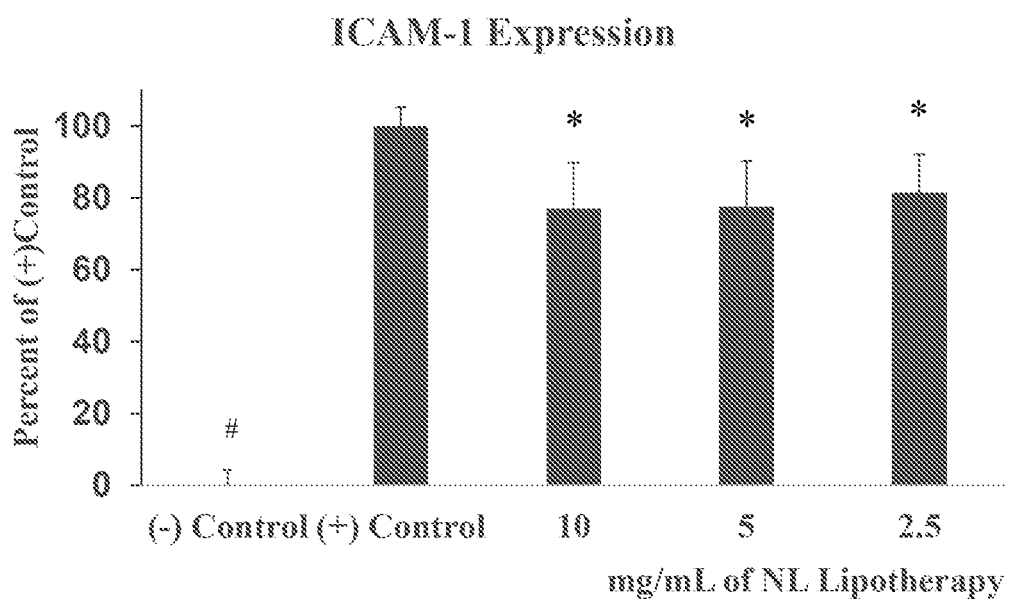

To determine whether NL lipotherapy reduces the activation of ECs, in vitro studies were performed on MCAECs cultured in 96-well plates. MCAECs were pre-treated for 20 min with 2.5, 5.0 or 10 mg/mL of NL lipid formulated with DOPC, DOPA, DOPE, 1.8:2.4:1 molar ratio, with 5% DHA and 0.5% S1P by weight, and cell activation was quantified by measuring ICAM-1 expression. A modified ELISA assay was used to quantify ICAM-1 expression using an Armenian hamster primary anti-mouse ICAM-1 antibody (Cat. No. MA5405) and a rabbit-anti-hamster secondary antibody (Cat. No. A18889) labeled with horse radish peroxidase (ThermoFisher Scientific, Grand Island, N.Y.). Six groups of MCAECs were studied: in Group 1, cells did not receive treatment (negative control); in Group 2, cells were treated with plastic contact activated plasma (positive control) for 2 h at 37° C.; in Groups 3-5 cells were pre-treated for 20 min with 2.5, 5.0 or 10.0 mg/mL of NL lipotherapy, and incubated with plastic contact activated plasma for 2 h at 37° C.; and in Group 6, cells were incubated with horse radish peroxidase-labeled antibodies to determine non-specific binding (background control). Plastic contact activated plasma was diluted with media at a 1:4 ratio. Activated plasma was washed out and cells were incubated with media for an additional 1 h prior to quantification of ICAM-1 expression. Experimental results demonstrated that pre-treatment of MCAECs with NL lipotherapy reduced ICAM-1 expression in all treated compared to the activated plasma control group (FIG. 4). In summary, these results suggest that NL lipotherapy attenuates the EC activation and expression of ICAM-1 when exposed to plastic contact activated plasma. If the NL lipotherapy has a similar effect in vivo, reducing the activation of ECs can attenuate the reperfusion-induced pro-inflammatory response that is in-part responsible for eliciting the no-reflow phenomenon.

Example 3. NL Lipotherapy has Low Toxicity

The NL lipotherapy lipid formulation can be considered natural since DOPC, DOPA, DOPE, DHA and SP are naturally occurring lipids in mammals and plants. However, to determine whether NL lipotherapy has potential toxic effects, we conducted in silico, in vitro and in vivo toxicity experiments. First, an in silico structure-activity relationship analysis examining DOPC and DOPA was performed to determine whether metabolites from these lipids could elicit any potential side effects. Second, we determined whether the fusion of NLs had a toxic effect on ECs, the primary target of the therapy. Lastly, we tested the toxicity of NL lipotherapy in vivo using a mouse model that received 3 to 4 times the normal dose of NL lipid.

Structure-Activity Relationship Analysis of NL Lipid Toxicity

An in silico analysis of the potential toxicity of lipids used in the instant NL formulation was performed using the cat-structure-activity relationship (cat-SAR). The cat-SAR program estimates the toxicological properties of chemicals, based on information from previously tested compounds. The method has been described in detail in several peer-reviewed publications.[47-49] The models are built for specific toxicological endpoints (e.g., carcinogenicity or genotoxicity) and describe the chemical substructures that differentiate between active and inactive chemicals for the endpoint of interests (e.g., carcinogens and non-carcinogens).

Table 1 lists the predicted toxicity values for each lipid as a probability of activity of all possible metabolites. The Cut-Off point values correspond to the Validation Results and are used to separate the probability of activity values to "positive" and "negative" calls. The first value is from a model with equal sensitivity and specificity and the second value is from a model with the best overall concordance between experimental and predicted results. In order to assess the toxicological potential of the NL lipids DOPC and DOPA, the cat-SAR models were adjusted for a balance between sensitivity and specificity. The results showed that DOPC and DOPA were inactive for salmonella mutagenicity, carcinogenic potency for rat cancer, human developmental toxicity, MCF-7 Relative Proliferate Effect (ESCREEN), and FDA National Center for Toxicological Research Estrogen Receptor Binding (NCTER ER). However, DOPC and DOPA were positive for mouse cancer; however, a positive mouse cancer finding is muted in the setting of negative findings for rat cancer and salmonella mutagenicity. The rationale is that a negative prediction of mutagenicity in the salmonella model goes against the notion of a metabolite being a mutagenic carcinogen.

TABLE 1

Prediction Overview Model

| | CUT-OFF Value | DOPC Pr(activity)/ Activity call | DOPA Pr(activity)/ Activity call |
|---|---|---|---|
| *Salmonella*, NTP Version date: 4/17/2009 Model parameters: (3/0.65/0.9) | 0.40 | 0.07/Inactive | 0.07/Inactive |
| Rat Cancer, CPDB Version date: 5/7/2010 Model parameters: (2/0.70/0.85) | 0.73 | 0.65/Inactive | 0.67/Inactive |
| Mouse Cancer, CPDB Version date: 6/7/2010 Model parameters: (4/0.65/0.80) | 0.64 | 0.79/Active | 0.79/Active |
| Human Developmental Toxicity Version date: 4/22/2009 Model parameters: (3/0.85/0.85) | 0.27 | 0.06/Inactive | 0.06/Inactive |
| Relative Proliferative Effect, ESCREEN Version date: 6/5/2009 Model parameters: (3/0.85/0.65) | 0.86 | 0.68/Inactive | 0.72/Inactive |
| Estrogen Receptor Binding, NCTRER Version date: 11/17/2009 Model parameters: (3/0.80/0.95) | 0.83 | 0.37/Inactive | 0.37/Inactive |

NL Lipotherapy Toxicity Studies were Performed In Vitro.

Figure 5:
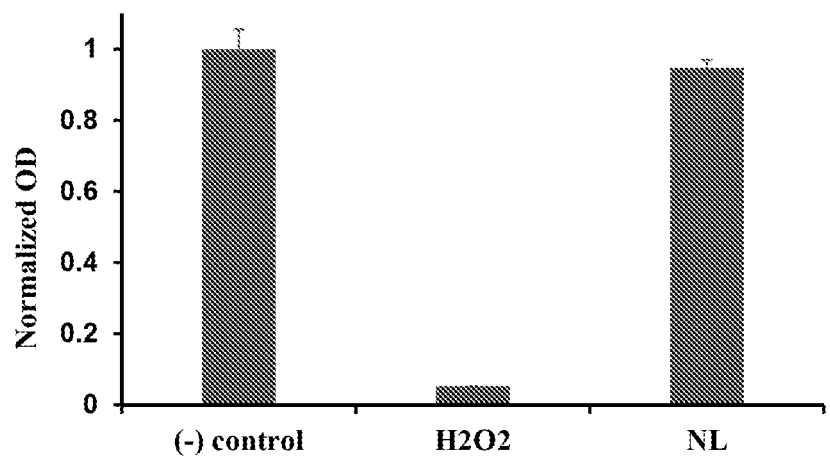
FIG. 5. Nanoliposome (NL) lipotherapy is not toxic to cells. In the negative (−) control group, cells were incubated in the medium only without any NL nor LPS treatment while in the $H_2O_2$ group (used as the positive control group), cells were treated with 5 mM $H_2O_2$ in the medium without NL nor LPS addition for 24 h. In the NL group, PCAECs were treated with NL lipotherapy (10 mg/mL of lipid) for 30 mins, then with the medium for 24 h at 37° C. NLs were formulated with DOPC, DOPA, DOPE, 1.8:2.4:1 molar ratio, with 5% DHA and 0.5% S1P by weight, hydrated with PBS. There was no difference between the (−) control and the treated group. These results indicate that NL fusion is not toxic to PCAECs. Values are mean±SEM, *P<0.05 vs. (−) control or NL.

To determine whether NL lipotherapy fusion to cells elicits any adverse effects on EC viability, PCAECs were incubated with NLs for 1 h. A viability assay using MTT [3-(4,5-dimethylthiazol-2-yl)-2,5-diphenyltetrazolium bromide] was conducted after 24 h post-treatment. Three groups of cells were studied: Group 1 was a negative (−) control in which cells received no treatment; Group 2 was a positive control in which cells were treated 5 mM of hydrogen peroxide ($H_2O_2$); and Group 3 were cells treated with NL lipotherapy. Experimental results demonstrated that treating cells with NL lipotherapy did not have an adverse effect on cell viability compared to untreated controls (FIG. 5). In summary, these results suggest that NL-to-cell fusion is not toxic to ECs.

Lipotherapy Toxicity Studies were Performed In Vivo

Figure 6:
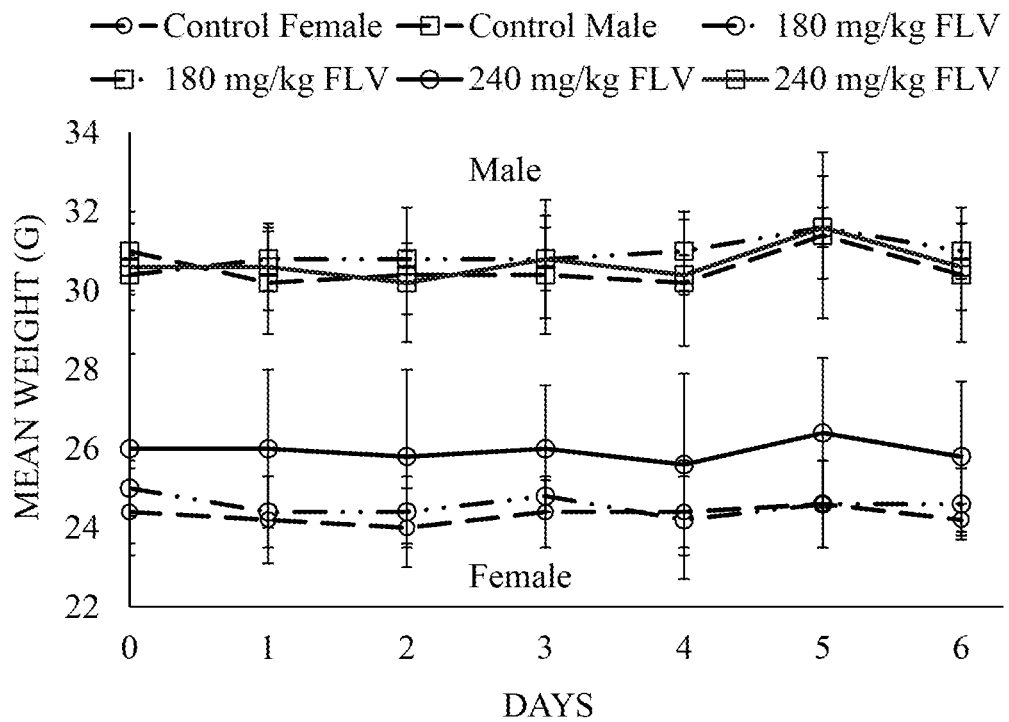
FIG. 6. Daily weight over a six-day period of female (red lines) and male (black lines) mice after a single injection of vehicle (PBS) or NL lipotherapy (DOPC, DOPA, DOPE, 1.8:2.4:1 molar ratio with 2% DHA by weight). Values are mean±SEM.

Webster male and female mice weighing ~30 g were administered 3 and 4 times the anticipated dose of lipotherapy. A single intravenous injection of 16 ml/kg vehicle had no effect on either female (Group 1A) or male (Group 1B) mouse weight (FIG. 6). Male mice had significantly higher globulin, white blood cell count, lymphocytes/ml and monocytes/ml; lower alkaline phosphatase, urea nitrogen, chlorine, cholesterol than female mice (See FIGS. 9-11).

A single intravenous injection with 180 mg/kg of a NL formulation (DOPC, DOPA, DOPE, 1.8:2.4:1 molar ratio with 2% DHA by weight) had no effect on either female (Group 2A) or male (Group 2B) mouse weight. No adverse effects were observed upon necropsy and no significant difference in clinical chemistry, complete blood counts, or differential white blood cell counts were recorded, relative to the vehicle-injected group (See FIGS. 9-11).

A single intravenous injection with 240 mg/kg of a NL formulation (DOPC, DOPA, DOPE, 1.8:2.4:1 molar ratio with 2% DHA by weight) (Group 3) had no effect on either female or male mouse weight. No adverse effects were observed upon necropsy. In the female mice (Group 3A) the total WBCs were significantly higher than in the vehicle treated group (1A), which was reflected in significantly more lymphocytes and monocytes. In the male mice (Group 3B) the clinical chemistry analysis yielded a significantly lower alkaline phosphatase value, than that observed in the vehicle treated mice (1B); this can be indicative of liver damage. These mice also exhibited a significantly higher percentage of circulating neutrophils, indicative of inflammation (See FIGS. 9-11).

Example 4. Intracoronary Lipotherapy Reduces Myocardial Injury in Pigs Following Coronary Occlusion Infarct expansion following PCI occurs during reperfusion and has been attributed primarily to endothelial dysfunction and the "no-reflow" phenomenon. NL lipotherapy is designed to rapidly deliver anti-inflammatory lipids to ECs and immune cells in blood, in order to reduce EC activation and attenuate endothelial barrier dysfunction during reperfusion. Using a pig myocardial infarction model, administration of intracoronary NL lipotherapy, with a formulation DOPC, DOPA, DOPE, 1.8:2.4:1 molar ratio, with 5% DHA and 0.5% S1P by weight, was tested to reduce infarct size. Female pigs weighing 20-30 kg were anesthetized and subjected to a 60 min occlusion of the left anterior descending (LAD) coronary artery using a balloon catheter. NL lipotheraphy (10 mL of a solution containing 10 mg/mL of lipid) or vehicle (Ringer's lactate) were administered via the lumen of the balloon catheter during the last 10 min of ischemia. Pigs were followed for 72 h post-infarction. Blood samples were collected at baseline, 2, 4 and 6 h of reperfusion, and analyzed for heart-specific fatty acid binding protein (hFABP), a biomarker of myocardial injury and microvascular no-reflow.[17] Infarct size and regional myocardial blood flow using microspheres were quantified.

Intracoronary NL Lipotherapy Reduces Heart Infarct Size in a Swine Model.

Figures 7A, 7B:
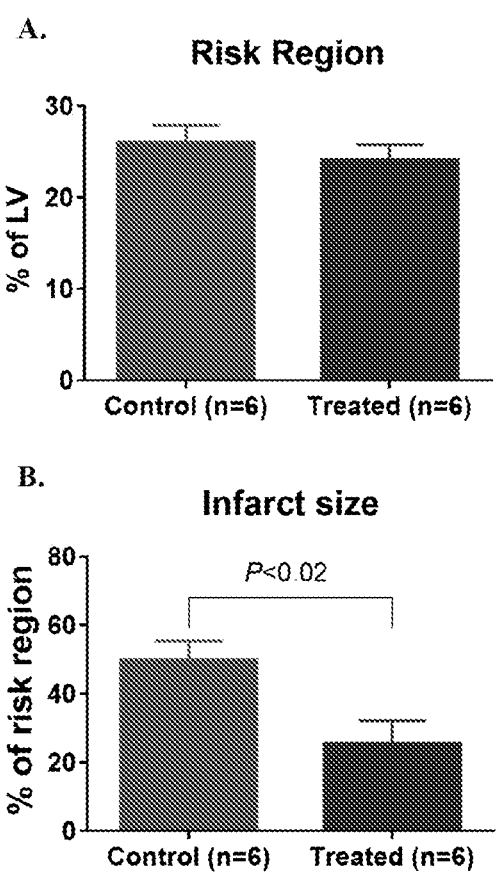
FIGS. 7A-7B Administration of intracoronary lipotherapy targeted to the microvascular endothelium of the area at risk reduces heart infarct size compared to controls. To create infarcts, a balloon catheter was placed in the left anterior descending coronary artery of swine and inflated for 60 min. Nanoliposome (NL) lipotherapy, formulated with DOPC, DOPA, DOPE, 1.8:2.4:1 molar ratio, with 5% DHA and 0.5% S1P by weight and hydrated with Ringer's Lactate, was administered during the last 10 min of occlusion via the lumen of the balloon catheter. Balloons were deflated and animals were followed for 72 h. Hearts were harvested and stained to quantify the risk region as a % of the left ventricle (A) and infarct size as a % of the risk region (B). Values are mean±SEM.

Myocardial infarction in pigs was induced by a 60-min balloon inflation followed by reperfusion with balloon deflation. Vehicle or NL lipotherapy solution (10 mL) was continuously infused at a rate of 1 mL/min into the occluded coronary artery bed via the central lumen of the balloon catheter, beginning at 50 min into the occlusion. The pigs were allowed to recover and followed for 72 h post-MI. The pigs were euthanized and the hearts were harvested and perfused with triphenyl tetrazolium chloride (TTC) and phthalo blue-dye to demarcate the infarct, ischemic, and non-ischemic tissue. The heart was sectioned into 6-7 slices, and fixed in formalin, and LV slices were photographed and analyzed to determine the infarct size, ischemic zone (IZ), and non-ischemic zone (NIZ). Thirteen pigs completed the protocol. Seven pigs received vehicle (Ringer's Lactate) and six received lipotherapy. One pig in the vehicle group was excluded due to hypothermia during the occlusion procedure (core body temperature was as low as 34° C., normal temperature is 40° C.). Thus, a total of 12 pigs (n=6 per group) were included in the final analysis. Efficacy of NL lipotherapy was assessed in terms of size of the "ischemic zone" (IZ) as % of LV and infarct size as % of risk region. Experimental results demonstrated that the risk region in the treatment and control groups was not different (FIG. 7A). The infarct size in hearts treated with NL lipotherapy was significantly smaller than in the control group (FIG. 7B). In summary, these findings suggest that NL lipotherapy administered following ischemia, just prior to reperfusion is effective in reducing myocardial infarct size.

Intracoronary NL Lipotherapy Administered to the Infarct Related Coronary Artery Improves Regional Myocardial Blood Flow (RMBF) in Risk Region Following Myocardial Infarction Myocardial infarction in pigs was induced by a 60-min balloon inflation followed by reperfusion with balloon deflation. Vehicle or NL lipotherapy solution (10 mL) was continuously infused at a rate of 1 mL/min into the occluded coronary artery bed via the central lumen of the balloon catheter, beginning at 50 min into the occlusion. Pigs were allowed to recover and followed for 72 h post-MI. RMBF was studied using neutron activated microspheres at baseline (before LAD occlusion), at 45 min into LAD occlusion and at 15 min and 72 h after reperfusion. Study results are shown in FIG. 12.

The experimental findings confirmed that there was no blood flow during balloon inflation in the ischemic zone (IZ) of controls and treated animals during LAD occlusion. These results suggest that the ischemia was complete and that the ischemic insult was equivalent for both groups. Also, the results demonstrated that the mean blood flow in the IZ after 15 min of reperfusion was 3-fold higher in the NL lipotherapy treated hearts compared to their adjacent non-ischemic zone (NIZ) and also compared to the IZ of the control group. In summary, these findings suggest that LAD occlusions were equivalent in the treatment and control groups. Administration of NL lipotherapy following LAD occlusion enhanced the microvascular blood flow during early reperfusion, suggesting that the therapy reduced or prevented the no-reflow phenomenon at this time point.

Figure 8:
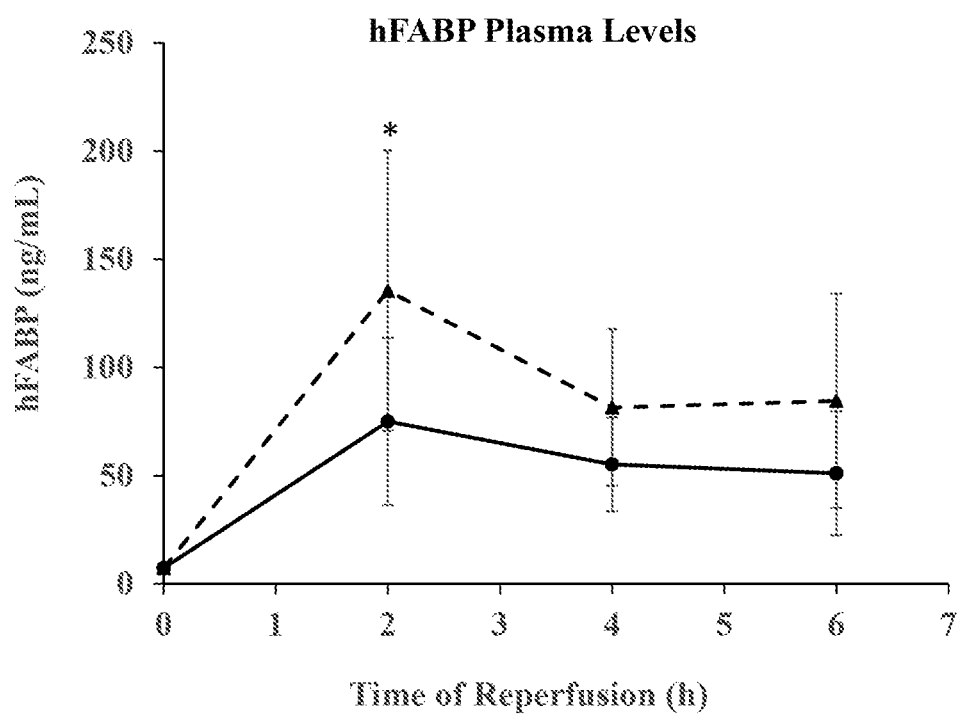
FIG. 8. Serial measurement of heart-specific fatty acid binding protein (hFABP) were performed on swine blood samples taken at baseline and during reperfusion following myocardial infarction. Plasma levels of hFABP were used as a biomarker for microvascular no-reflow in the risk region following reperfusion of the occluded coronary artery. Levels of hFABP were compared between animals receiving intracoronary infusion of NL lipotherapy (circles) or vehicle (Ringer's lactate) control (triangles). The results demonstrated that levels of serum hFABP peaked at two hours of reperfusion in both groups. There was a significance difference in hFABP levels between NL lipotherapy treated and vehicle treated swine. These results suggest that microvascular no-reflow was diminished in the NL lipotherapy treated hearts. Values are mean±SD; *P-value<0.05 vs. vehicle.

Intracoronary NL Lipotherapy Administered to the Infarct Related Coronary Artery Reduces Serum hFABP Levels, a Serum Biomarker of Microvascular No-Reflow Plasma levels of hFABP were quantified using a Pig Cardiac FABP ELISA kit (Cat. No. HFABP-9, Life Diagnostics, Westchester, Pa.) Experimental findings demonstrated that administration of NL lipotherapy into the infarct related artery significantly reduced plasma levels of hFABP at 2 hours of reperfusion compare to vehicle (Ringer's lactate) treated hearts (FIG. 8). Although plasma hFABP levels at 1 h of reperfusion correlate best to quantify no-reflow,[17] the 2-hour hFABP levels were significantly reduced in hearts treated with NL lipotherapy, suggesting a lower occurrence of microvascular no-reflow. In conclusion, the combination of findings for the biomarker hFABP, RMBF during early reperfusion and infarct size at 72 h suggest that NL lipotherapy attenuated reperfusion-associated endothelial dysfunction and no-reflow; enhancing myocardial viability.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

LITERATURE CITED

1. McAlindon E, Bucciarelli-Ducci C, Suleiman M S and Baumbach A. Infarct size reduction in acute myocardial infarction. *Heart.* 2015; 101:155-60.
2. Francone M, Bucciarelli-Ducci C, Carbone I, Canali E, Scardala R, Calabrese F A, Sardella G, Mancone M, Catalano C, Fedele F, Passariello R, Bogaert J and Agati L. Impact of primary coronary angioplasty delay on myocardial salvage, infarct size, and microvascular damage in patients with ST-segment elevation myocardial infarction: insight from cardiovascular magnetic resonance. *J Am Coll Cardiol.* 2009; 54:2145-53.
3. Reffelmann T and Kloner R A. The "no-reflow" phenomenon: basic science and clinical correlates. Heart. 2002; 87:162-8.
4. Feher A, Chen S Y, Bagi Z and Arora V. Prevention and treatment of no-reflow phenomenon by targeting the coronary microcirculation. *Rev Cardiovasc Med.* 2014; 15:38-51.
5. State Program Injury Indicators Report, Fourth Edition 2005 Data. CDC and NCIPC Publication. 0.2099.
6. Rezkalla S H, Stankowski R V, Hanna J and Kloner R A. Management of No-Reflow Phenomenon in the Catheterization Laboratory. *JACC Cardiovasc Interv.* 2017; 10:215-223.
7. Mahaffey K W, Puma J A, Barbagelata N A, DiCarli M F, Leesar M A, Browne K F, Eisenberg P R, Bolli R, Casas A C, Molina-Viamonte V, Orlandi C, Blevins R, Gibbons R J, Califf R M and Granger C B. Adenosine as an adjunct to thrombolytic therapy for acute myocardial infarction: results of a multicenter, randomized, placebo-controlled trial: the Acute Myocardial Infarction STudy of ADenosine (AMISTAD) trial. *J Am Coll Cardiol.* 1999; 34:1711-20.
8. Ross A M, Gibbons R J, Stone G W, Kloner R A, Alexander R W and Investigators A-I. A randomized, double-blinded, placebo-controlled multicenter trial of adenosine as an adjunct to reperfusion in the treatment of acute myocardial infarction (AMISTAD-II). *J Am Coll Cardiol.* 2005; 45:1775-80.
9. Durante A and Camici P G. Novel insights into an "old" phenomenon: the no reflow. *Int J Cardiol.* 2015; 187:273-80.
10. Bolognese L, Carrabba N, Parodi G, Santoro G M, Buonamici P, Cerisano G and Antoniucci D. Impact of microvascular dysfunction on left ventricular remodeling and long-term clinical outcome after primary coronary angioplasty for acute myocardial infarction. *Circulation.* 2004; 109:1121-6.
11. Huang R I, Patel P, Walinsky P, Fischman D L, Ogilby J D, Awar M, Frankil C and Savage M P. Efficacy of intracoronary nicardipine in the treatment of no-reflow during percutaneous coronary intervention. *Catheter Cardiovasc Interv.* 2006; 68:671-6.
12. Iwakura K, Ito H, Okamura A, Koyama Y, Date M, Higuchi Y, Inoue K, Kimura R, Nagai H, Imai M, Toyoshima Y, Ozawa M, Ito N, Okazaki Y, Shibuya M, Suenaga H, Kubota A and Fujii K. Nicorandil treatment in patients with acute myocardial infarction: a meta-analysis. *Circ J.* 2009; 73:925-31.
13. Zeng Y, Adamson R H, Curry F R and Tarbell J M. Sphingosine-1-phosphate protects endothelial glycocalyx by inhibiting syndecan-1 shedding. *Am J Physiol Heart Circ Physiol.* 2014; 306:H363-72.
14. Bode C, Sensken S C, Peest U, Beutel G, Thol F, Levkau B, Li Z, Bittman R, Huang T, Tolle M, van der Giet M and Graler M H. Erythrocytes serve as a reservoir for cellular and extracellular sphingosine 1-phosphate. *J Cell Biochem.* 2010; 109:1232-43.
15. Blaho V A and Hla T. An update on the biology of sphingosine 1-phosphate receptors. *Journal of lipid research.* 2014; 55:1596-608.

16. Hanson M A, Roth C B, Jo E, Griffith M T, Scott F L, Reinhart G, Desale H, Clemons B, Cahalan S M, Schuerer S C, Sanna M G, Han G W, Kuhn P, Rosen H and Stevens R C. Crystal structure of a lipid G protein-coupled receptor. *Science*. 2012; 335:851-5.

17. Uitterdijk A, Sneep S, van Duin R W, Krabbendam-Peters I, Gorsse-Bakker C, Duncker D J, van der Giessen W J and van Beusekom H M. Serial measurement of hFABP and high-sensitivity troponin I post-PCI in STEMI: how fast and accurate can myocardial infarct size and no-reflow be predicted? *Am J Physiol Heart Circ Physiol*. 2013; 305:H1104-10.

What is claimed is:

1. A method for treating microvascular dysfunction, the method consisting of administering, to a subject in need thereof, an effective amount of nanoliposomes consisting of one or more negatively charged phospholipids, one or more neutrally charged phospholipids, a polyunsaturated fatty acid (PUFA) and a lysosphingolipid,
    wherein the neutrally charged phospholipids are selected from the group consisting of phosphatidylcholine (PC) and phosphatidylethanolamine (PE), or a combination thereof, and the negatively charged phospholipids are selected from the group consisting of phosphatidic acid (PA), phosphatidylserine (PS), and phosphatidylgylcerol (PG), or a combination thereof, wherein within 15 minutes of exposure to endothelial cells, at least 5% nanoliposomes are bound or fused to the endothelial cells,
    wherein the PUFA in the nanoliposomes constitutes 1%-5% of the nanoliposomes by weight and the lysosphingolipid in the nanoliposomes constitutes 0.1%-0.5% of the nanoliposomes by weight.

2. The method of claim 1, wherein the composition is administered to the subject intra-arterially while a catheter is positioned in the ischemia related artery prior to the formation of the anatomic zone of no-reflow.

3. The method of claim 1, wherein the composition is administered into the anatomic zone of no-reflow by using Ringer's lactate at physiological pH as the vehicle.

4. A method for inhibiting endothelial cell or immune cell activation, the method consisting of
    administering a therapeutic effective amount of a composition consisting of one or more negatively charged phospholipids, one or more neutrally charged phospholipids, a polyunsaturated fatty acid (PUFA) and a lysosphingolipid, to a subject in need thereof, wherein the composition is administered via intra-arterial delivery, wherein the PUFA in the nanoliposomes constitutes 1%-5% of the nanoliposomes by weight and the lysosphingolipid in the nanoliposomes constitutes 0.1%-0.5% of the nanoliposomes by weight.

5. A method for inhibiting endothelial cell activation, the method consisting of administering to a subject in need thereof a plurality of nanoliposomes consisting of one or more negatively charged phospholipids, one or more neutrally charged phospholipids, a polyunsaturated fatty acid (PUFA) and a lysosphingolipid,
    wherein the neutrally charged phospholipids are selected from the group consisting of phosphatidylcholine (PC) and phosphatidylethanolamine (PE), or a combination thereof, and the negatively charged phospholipids are selected from the group consisting of phosphatidic acid (PA), phosphatidylserine (PS), and phosphatidylgylcerol (PG), or a combination thereof,
    wherein within 15 minutes of exposure to endothelial cells, at least 5% nanoliposomes are bound or fused to the endothelial cells, wherein the PUFA in the nanoliposomes constitutes 1%-5% of the nanoliposomes by weight and the lysosphingolipid in the nanoliposomes constitutes 0.1%-0.5% of the nanoliposomes by weight.

6. The method of claim 4, wherein the method inhibits endothelial cell or immune cell activation through adjusting the cell membrane lipid composition.

7. The method of claim 4, wherein the method inhibits inflammatory responses of immune cells.

8. The method of claim 4, wherein the method inhibits the inflammatory responses of macrophages.

* * * * *